US011827631B2

(12) United States Patent
Druzgala et al.

(10) Patent No.: US 11,827,631 B2
(45) Date of Patent: *Nov. 28, 2023

(54) METHODS FOR THE TREATMENT OF GASTRO-INTESTINAL DISORDERS

(71) Applicant: Renexxion, LLC, Los Altos, CA (US)

(72) Inventors: Pascal Jean Druzgala, Santa Rosa, CA (US); Peter Milner, Mountain View, CA (US)

(73) Assignee: Renexxion, LLC, Los Altos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/157,783

(22) Filed: Jan. 20, 2023

(65) Prior Publication Data

US 2023/0339933 A1  Oct. 26, 2023

Related U.S. Application Data

(60) Division of application No. 17/887,325, filed on Aug. 12, 2022, now Pat. No. 11,643,409, which is a continuation of application No. 16/734,961, filed on Jan. 6, 2020, now Pat. No. 11,498,918, which is a division of application No. 16/181,177, filed on Nov. 5, 2018, now Pat. No. 10,570,127.

(51) Int. Cl.
| | |
|---|---|
| *A61K 9/00* | (2006.01) |
| *A61P 1/10* | (2006.01) |
| *A61P 1/04* | (2006.01) |
| *A61K 31/439* | (2006.01) |
| *C07D 453/02* | (2006.01) |

(52) U.S. Cl.
CPC .......... *C07D 453/02* (2013.01); *A61K 9/0029* (2013.01); *A61K 9/0053* (2013.01); *A61K 31/439* (2013.01); *A61P 1/04* (2018.01); *A61P 1/10* (2018.01); *C07B 2200/13* (2013.01)

(58) Field of Classification Search
CPC .......................... C07D 453/02; C07B 2200/13
See application file for complete search history.

(56) References Cited

U.S. PATENT DOCUMENTS

| | | | |
|---|---|---|---|
| 3,536,809 | A | 10/1970 | Applezweig et al. |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 4,962,115 | A | 10/1990 | Van Daele |
| 5,057,525 | A | 10/1991 | Van Daele |
| 6,331,401 | B1 | 12/2001 | Gerald et al. |
| 6,552,046 | B2 | 4/2003 | Druzgala et al. |
| 6,632,827 | B2 | 10/2003 | McCULLOUGH et al. |
| 7,176,218 | B2 | 2/2007 | Irwin et al. |
| 7,282,509 | B2 | 10/2007 | Irwin et al. |
| 7,326,787 | B2 | 2/2008 | By et al. |
| 7,629,466 | B2 | 12/2009 | By et al. |
| 8,138,204 | B2 | 3/2012 | Irwin et al. |
| 8,524,736 | B2 | 9/2013 | Irwin et al. |
| 10,570,127 | B1 | 2/2020 | Druzgala et al. |
| 11,498,918 | B2 | 11/2022 | Druzgala et al. |
| 11,643,409 | B2 | 5/2023 | Druzgala et al. |
| 2005/0176757 | A1 | 8/2005 | Irwin et al. |
| 2005/0197363 | A1 | 9/2005 | Irwin et al. |
| 2007/0078265 | A1 | 4/2007 | By et al. |
| 2008/0076927 | A1 | 3/2008 | By et al. |
| 2008/0085921 | A1 | 4/2008 | Irwin et al. |
| 2009/0137810 | A1 | 5/2009 | By et al. |
| 2013/0040987 | A1 | 2/2013 | Irwin et al. |
| 2020/0255420 | A1 | 8/2020 | Druzgala et al. |
| 2021/0355116 | A1 | 11/2021 | Druzgala et al. |
| 2022/0380361 | A1 | 12/2022 | Druzgala et al. |

FOREIGN PATENT DOCUMENTS

| | | | |
|---|---|---|---|
| EP | | 0640601 A1 | 3/1995 |
| TW | | I304067 B | 12/2008 |
| WO | WO-2001093849 A2 | | 12/2001 |
| WO | WO-2004000840 A2 | | 12/2003 |

(Continued)

OTHER PUBLICATIONS

Barnes N.M., et al. "Identification of 5-HT.sub.3 Recognition Sites in the Ferret Area Postrema," Journal of Pharmacy and Pharmacology, Apr. 5, 1998, vol. 40, pp. 586-588.

Braun D.E., et al., "Insights into Hydrate Formation and Stability of Morphinanes from a Combination of Experimental and Computational Approaches," Molecular Pharmaceutics, Jul. 18, 2014, vol. 11, pp. 3145-3163.

Decktor D.L., et al., "Effect Of Metoclopramide, Bethanechol And The Cholecystokinin Receptor Antagonist, L-364,718, On Gastric Emptying In The Rat," European Journal of Pharmacology, Mar. 1988, vol. 147, pp. 313-316.

Hoffman J.M., et al., "Activation of Colonic Mucosal 5-HT4 Receptors Accelerates Propulsive Motility and Inhibits Visceral Hypersensitivity," Gastroenterology, Apr. 2012, vol. 142 (4), pp. 844-854.

(Continued)

*Primary Examiner* — Susanna Moore
(74) *Attorney, Agent, or Firm* — Cooley LLP

(57) ABSTRACT

Provided herein is a bulk composition comprising the trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt. Provided are also pharmaceutical compositions and dosage forms comprising the trihydrate form, and methods and uses for treating a gastrointestinal disorder in a subject with the trihydrate form. In some embodiments, the gastrointestinal disorder is gastroesophageal reflux disease (GERD), dyspepsia (such as functional dyspepsia or functional motility disorder), gastroparesis, paralytic ileus, post-operative ileus, emesis, nausea, heartburn, intestinal pseudo-obstruction, irritable bowel syndrome (IBS), constipation, enteral feeding intolerance (EFI), or esophagitis. In some embodiments, the gastrointestinal disorder is post-operative ileus, chronic grass sickness, constipation, megacolon, gastritis, gastrointestinal stasis, or abomasal emptying defect.

34 Claims, 5 Drawing Sheets

(56) References Cited

FOREIGN PATENT DOCUMENTS

| WO | WO-2005068461 A1 | 7/2005 |
| WO | WO-2007028073 A2 | 3/2007 |
| WO | WO-2010062959 A1 | 6/2010 |
| WO | WO-2013024164 A1 | 2/2013 |
| WO | WO-2018153890 A1 | 8/2018 |
| WO | WO-2020096909 A1 | 5/2020 |
| WO | WO-2020096911 A1 | 5/2020 |

OTHER PUBLICATIONS

International Preliminary Report on Patentability for PCT/US2019/059513, dated May 11, 2021, 6 pages.

International Preliminary Report on Patentability for PCT/US2019/059517, dated May 11, 2021, 7 pages.

International Search Report and Written Opinion for International Application No. PCT/US2005/000510, dated Jun. 29, 2005, 12 Pages.

International Search Report and Written Opinion for PCT/US2006/034322, dated Feb. 20, 2007, 10 pages.

International Search Report and Written Opinion for PCT/US2019/059513 dated Mar. 19, 2020, 12 pages.

International Search Report and Written Opinion for PCT/US2019/059517 dated Mar. 17, 2020, 12 pages.

Non-Final Office Action for U.S. Appl. No. 17/245,466 dated Sep. 2, 2022, 21 pages.

Non-Final Office Action for U.S. Appl. No. 17/887,325, dated Oct. 24, 2022, 7 pages.

Notice of Allowance for U.S. Appl. No. 16/734,961 dated Sep. 2, 2022, 8 pages.

Notice of Allowance for U.S. Appl. No. 17/887,325, dated Jan. 10, 2023, 5 pages.

Stacher G., et al., "Effects of Oral Cisapride on Interdigestive Jejunal Motor Activity, Psychomotor Function, and Side-Effect Profile in Healthy Man," Digestive Diseases and Sciences, Nov. 1987, vol. 32 (11), pp. 1223-1230.

U.S. Appl. No. 62/755,973, filed Nov. 5, 2018, by Druzgala et al. (unpublished).

Co-pending U.S. Appl. No. 18/363,600, inventors Druzgala; Pascal Jean et al., filed Aug. 1, 2023.

International Preliminary Report on Patentability for International Application No. PCT/US2005/000510, dated Jul. 10, 2006, 8 pages.

International Preliminary Report on Patentability for International Application No. PCT/US2006/034322, dated Mar. 4, 2008, 9 pages.

Van Daele et al., "Synthesis of cisapride, a gastrointestinal stimulant derived from cis-4-amino-3-methoxypiperidine". Drug Development Res. (May-Aug. 1986); 8 (1-4): 225-232.

Wilen, S.H. et al., "Strategies in Optical Resolutions". Tetrahedron (1977); 33: 2725-2736.

METHODS FOR THE TREATMENT OF GASTRO-INTESTINAL DISORDERS

CROSS-REFERENCE TO RELATED APPLICATIONS

This application is a divisional application of U.S. application Ser. No. 17/887,325, filed Aug. 12, 2022, now U.S. Pat. No. 11,643,409, which is a continuation application of U.S. application Ser. No. 16/734,961, filed Jan. 6, 2020, now U.S. Pat. No. 11,498,918, which is a divisional application of U.S. application Ser. No. 16/181,177, filed Nov. 5, 2018, now U.S. Pat. No. 10,570,127, each of which is hereby incorporated by reference in its entirety.

FIELD

The present disclosure relates to bulk compositions and pharmaceutical compositions comprising a trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt, and methods of treating gastrointestinal disorders with this form.

BACKGROUND

Benzamide derivatives and pharmaceutically acceptable salts thereof can act as stimulators of gastrointestinal motility. Many of these compounds are also antagonists of the dopamine D2 receptor, which also plays an important role in the gastrointestinal system. Dopaminergic effects in the gastrointestinal system may include nausea and vomiting. Thus, some of these benzamides are effective anti-emetic agents and they may be used to control vomiting during cancer chemotherapy or radiotherapy, especially when highly emetogenic compounds such as cisplatin are used. This anti-emetic action is believed to be the result of the ability of the benzamides to block the actions of serotonin (5HT) at specific sites of action, called the $5HT_3$-receptor.

A second prominent action of some benzamide derivatives is in augmenting gastrointestinal smooth muscle activity from the esophagus through the proximal small bowel, thus accelerating esophageal and small intestinal transit as well as facilitating gastric emptying and increasing lower esophageal sphincter tone. It is currently believed that the primary smooth muscle effects of some benzamide derivatives are the result of an agonist action upon a class of serotonin receptors referred to as $5HT_4$ receptors, which are located on interneurons in the myenteric plexus of the gut wall.

The benzamide Cisapride, a potent $5$-$HT_4$ agonist, was introduced more than 20 years ago and it has been used primarily to treat gastroesophageal reflux disease (GERD). Other $5$-$HT_4$ agonists of the benzamide class were subsequently introduced to patients. Because of their activity as prokinetic agents, some $5$-$HT_4$ agonists also appear to be useful to treat dyspepsia, gastroparesis, constipation, post-operative ileus, and intestinal pseudo-obstruction.

However, many of these compounds, including Cisapride, are associated with serious cardiac arrhythmias, such as ventricular tachycardia, ventricular fibrillation, torsades de pointer, and QT prolongation. The safety of $5HT_4$ receptor agonists may also be limited by adverse drug interactions due to hepatic cytochrome P-450 metabolism. Thus, what is needed in the art are benzamide $5$-$HT_4$ agonists that have a lower incidence of cardiac arrhythmias, which may be used to treat gastrointestinal disorders.

Naronapride ((3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt) is an orally bioavailable selective serotonin $5$-$HT_4$ receptor agonist that has been shown in animals and in humans to be safe for use in treating gastrointestinal disorders, and has a low incidence of adverse cardiovascular effects. See U.S. Pat. Nos. 7,176,218; 7,282,509; 7,326,787; 7,629,466; 8,138,204; and 8,524,736, incorporated herein by reference in their entireties.

What is needed in the art are improved forms of naronapride for clinical use, and methods of producing bulk compositions thereof.

BRIEF SUMMARY

In some aspects, provided herein is a bulk composition comprising a trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt, which has the following formula:

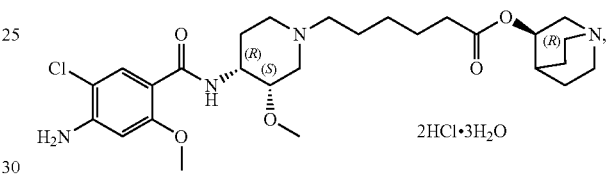

and at least one container.

In other aspects, provided herein is a pharmaceutical composition comprising a trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt, which has the following formula:

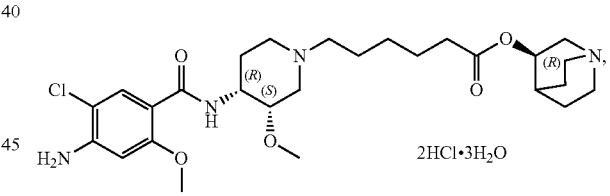

and a pharmaceutically acceptable excipient.

In certain aspects, provided herein is a dosage form that includes the pharmaceutical composition.

Also provided herein is a method of treating a gastrointestinal disorder in a subject in need thereof, which includes administering to the subject in need thereof a therapeutically effective amount of a pharmaceutical composition provided herein, or a dosage form provided herein, comprising the trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt. In some embodiments, the gastrointestinal disorder is selected from the group consisting of gastroesophageal reflux disease (GERD), functional dyspepsia or functional motility disorder, gastroparesis, paralytic ileus, post-operative ileus, emesis, nausea, heartburn, intestinal pseudo-obstruction, irritable bowel syndrome (IBS), constipation, enteral feeding intolerance (EFI), and esophagitis. In some embodiments, the subject in need thereof is a human.

In other embodiments, the gastrointestinal disorder is selected from the group consisting of post-operative ileus, chronic grass sickness, constipation, megacolon, gastritis, gastrointestinal stasis, and abomasal emptying defect. In some embodiments, the subject in need thereof is a non-human animal, such as a ruminant, an equine, a cat, a dog, a rabbit, or a guinea pig.

In other embodiments, provided herein is the use of a trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt in the manufacture of a medicament for treating a gastrointestinal disorder in a subject in need thereof. In some embodiments, the gastrointestinal disorder is selected from the group consisting of gastroesophageal reflux disease (GERD), functional dyspepsia or functional motility disorder, gastroparesis, paralytic ileus, post-operative ileus, emesis, nausea, heartburn, intestinal pseudo-obstruction, irritable bowel syndrome (IBS), constipation, enteral feeding intolerance (EFI), and esophagitis. In some embodiments, the subject in need thereof is a human. In other embodiments, the gastrointestinal disorder is selected from the group consisting of post-operative ileus, chronic grass sickness, constipation, megacolon, gastritis, gastrointestinal stasis, and abomasal emptying defect. In some embodiments, the subject in need thereof is a non-human animal, such as a ruminant, an equine, a cat, a dog, a rabbit, or a guinea pig.

In still other aspects, provided herein is a compound, or pharmaceutical composition comprising a compound, for use in treating a gastrointestinal disorder in a subject in need thereof, wherein the compound is a trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt. In some embodiments, the gastrointestinal disorder is selected from the group consisting of gastroesophageal reflux disease (GERD), functional dyspepsia or functional motility disorder, gastroparesis, paralytic ileus, post-operative ileus, emesis, nausea, heartburn, intestinal pseudo-obstruction, irritable bowel syndrome (IBS), constipation, enteral feeding intolerance (EFI), and esophagitis. In some embodiments, the subject in need thereof is a human. In other embodiments, the gastrointestinal disorder is selected from the group consisting of post-operative ileus, chronic grass sickness, constipation, megacolon, gastritis, gastrointestinal stasis, and abomasal emptying defect. In some embodiments, the subject in need thereof is a non-human animal, such as a ruminant, an equine, a cat, a dog, a rabbit, or a guinea pig.

In other aspects, provided herein is a method of improving gastrointestinal motility in a subject in need thereof, which includes administering to the subject in need thereof a therapeutically effective amount of a pharmaceutical composition provided herein, or a dosage form provided herein, comprising the trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt. In some embodiments, the subject in need thereof has a gastrointestinal disorder. In some embodiments, the gastrointestinal disorder is selected from the group consisting of gastroesophageal reflux disease (GERD), functional dyspepsia or functional motility disorder, gastroparesis, paralytic ileus, post-operative ileus, emesis, nausea, heartburn, intestinal pseudo-obstruction, irritable bowel syndrome (IBS), constipation, enteral feeding intolerance (EFI), and esophagitis. In some embodiments, the subject in need thereof is a human. In other embodiments, the gastrointestinal disorder is selected from the group consisting of post-operative ileus, chronic grass sickness, constipation, megacolon, gastritis, gastrointestinal stasis, and abomasal emptying defect. In some embodiments, the subject in need thereof is a non-human animal, such as a ruminant, an equine, a cat, a dog, a rabbit, or a guinea pig.

In other embodiments, provided herein is the use of a trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt in the manufacture of a medicament for improving gastrointestinal motility in a subject in need thereof. In some embodiments, the subject in need thereof has a gastrointestinal disorder selected from the group consisting of gastroesophageal reflux disease (GERD), functional dyspepsia or functional motility disorder, gastroparesis, paralytic ileus, post-operative ileus, emesis, nausea, heartburn, intestinal pseudo-obstruction, irritable bowel syndrome (IBS), constipation, enteral feeding intolerance (EFI), and esophagitis. In some embodiments, the subject in need thereof is a human. In other embodiments, the gastrointestinal disorder is selected from the group consisting of post-operative ileus, chronic grass sickness, constipation, megacolon, gastritis, gastrointestinal stasis, and abomasal emptying defect. In some embodiments, the subject in need thereof is a non-human animal, such as a ruminant, an equine, a cat, a dog, a rabbit, or a guinea pig.

In still other aspects, provided herein is a compound, or pharmaceutical composition comprising a compound, for use in improving gastrointestinal motility in a subject in need thereof, wherein the compound is a trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt. In some embodiments, the subject in need thereof has a gastrointestinal disorder. In some embodiments, the gastrointestinal disorder is selected from the group consisting of gastroesophageal reflux disease (GERD), functional dyspepsia or functional motility disorder, gastroparesis, paralytic ileus, post-operative ileus, emesis, nausea, heartburn, intestinal pseudo-obstruction, irritable bowel syndrome (IBS), constipation, enteral feeding intolerance (EFI), and esophagitis. In some embodiments, the subject in need thereof is a human. In other embodiments, the gastrointestinal disorder is selected from the group consisting of post-operative ileus, chronic grass sickness, constipation, megacolon, gastritis, gastrointestinal stasis, and abomasal emptying defect. In some embodiments, the subject in need thereof is a non-human animal, such as a ruminant, an equine, a cat, a dog, a rabbit, or a guinea pig.

DETAILED DESCRIPTION

Figure 1:
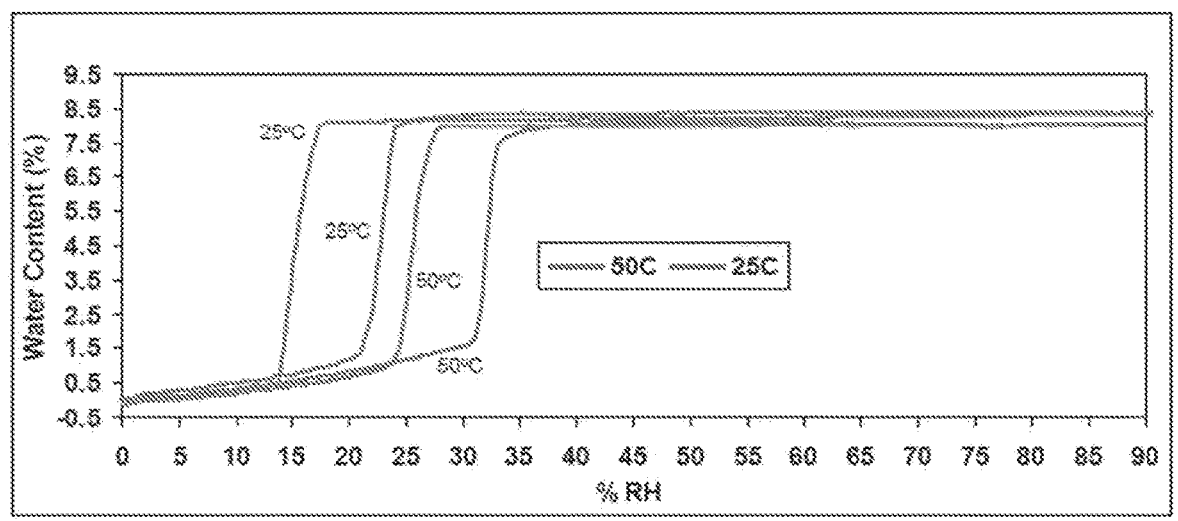
FIG. 1 is a water vapor sorption isotherm of the di-hydrochloride salt at 25° C. (two left lines) and 50° C. (two right lines).
Figure 2:
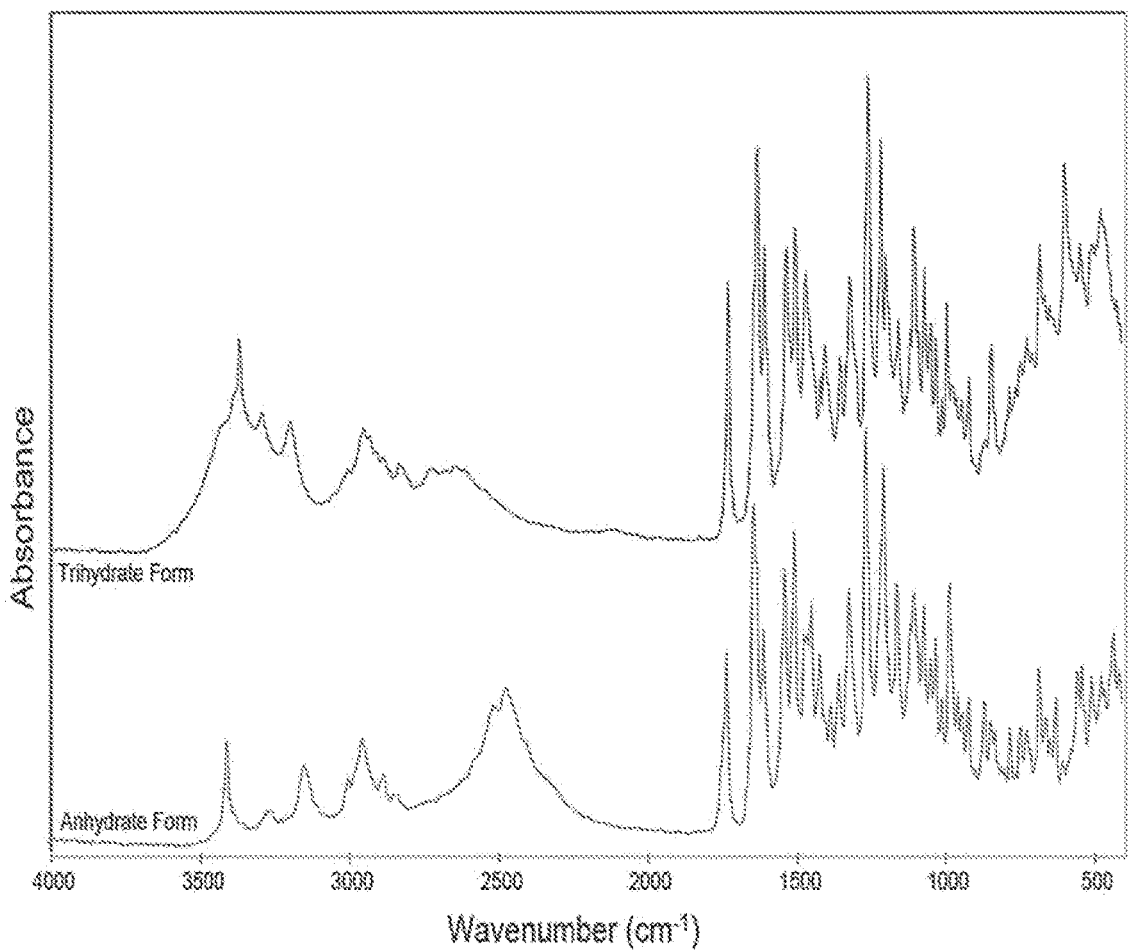
FIG. 2 are Fourier transform infrared (FTIR) spectra of the anhydrate and the trihydrate forms of the (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt.

Provided herein is a trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt (Compound 1), which has the following formula:

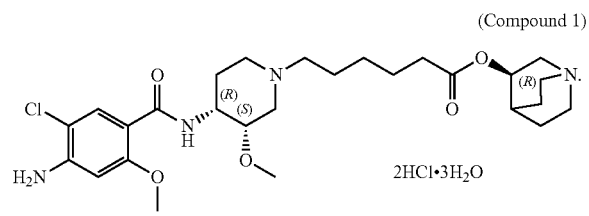

(Compound 1)

2HCl·3H$_2$O

Also provided herein are bulk compositions comprising Compound 1, and a container. In other aspects, provided herein is a pharmaceutical composition comprising Compound 1 and a pharmaceutically acceptable excipient. Further provided herein are methods of treating a disorder in a subject in need thereof, comprising administering to the subject in need thereof a therapeutically effective amount of Compound 1, or a pharmaceutical composition comprising a therapeutically effective amount of Compound 1; and the use of Compound 1, or a pharmaceutical composition comprising Compound 1, in treating a disorder in a subject in need thereof; and the use of Compound 1 in the manufacture of a medicament for treating a disorder in a subject in need thereof.

I. Compound 1

It has been surprisingly found that the di-hydrochloride salt of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester can exist in a trihydrate form. The trihydrate form (Compound 1) has many advantages over the anhydrous form, including tolerance of a broader range of storage conditions and the ability to be formulated with hydrated and/or hygroscopic excipients. The difference in formula weights between the anhydrous form (FW=610.01 g/mol) and the trihydrate (FW=664.06 g/mol) would result in an approximately 8% to 9% deficit in a final formulation if the wrong form is used (e.g., using the trihydrate when the anhydrous is intended, or the anhydrous when the trihydrate is intended). Thus, provided herein are also X-ray powder diffraction peaks which may, in some embodiments, be used to identify which form is present in a composition.

A. X-Ray Powder Diffraction (XRPD)

In some embodiments, Compound 1 (including the Compound 1 in the bulk compositions, pharmaceutical compositions, dosage forms, kits, or medicaments comprising any of these as provided herein) is in a crystalline form, and the crystalline form has XRPD 2-theta (2θ) peaks at: 7.74° 0.5° (>50% relative intensity), and 20.95°±0.5° (100% relative intensity). In some embodiments, Compound 1 has XRPD 2-theta (2θ) peaks at: 7.6°±0.2° (>50% relative intensity), and 20.7°±0.2° (100% relative intensity). In other embodiments, Compound 1 is in an amorphous form.

In some embodiments, Compound 1 is in a crystalline form, and the crystalline form has XRPD peaks at (degrees 2-theta (2θ)) 7.74°±0.5°, and 20.95°±0.5°, and at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, or each of the XRPD 2-theta (2θ) peaks selected from the group consisting of 10.3°±0.2°, 13.6°±0.2°, 14.8°±0.2°, 15.0°±0.2°, 15.4°±0.2°, 17.5°±0.2°, 18.3°±0.2°, 18.6°±0.2°, 19.2°±0.2°, 21.3°±0.2° 0, 22.0°±0.2°, 23.6°±0.2°, 24.3°±0.2°, 25.2°±0.2°, 26.0°±0.2°, 27.2°±0.2°, 30.1°±0.2°, 32.4°±0.2°, 33.4°±0.2°, 38.2°±0.2°, and 39.4°±0.2°.

In some embodiments, Compound 1 is in a crystalline form, and the crystalline form has XRPD 2-theta (2θ) peaks at 7.6°±0.2°, 10.3°±0.2°, and 20.7°±0.2°. In certain embodiments, Compound 1 is in a crystalline form, and the crystalline form has XRPD 2-theta (2θ) peaks at 7.6°+0.2°, 10.3°±0.2°, 19.2°±0.2°, and 20.7°±0.2°. In other embodiments, Compound 1 is in a crystalline form, and the crystalline form has XRPD 2-theta (2θ) peaks at 7.6°±0.2°, 10.3°±0.2°, 19.2°±0.2°, 20.7°±0.2°, and 33.4°±0.2°. In still further embodiments, Compound 1 is in a crystalline form, and the crystalline form has XRPD 2-theta (2θ) peaks at 7.6°±0.2°, 10.3°±0.2°, 19.2°±0.2°, 20.7°±0.2°, 33.4°±0.2°, and 38.2°±0.2°. In some embodiments, Compound 1 is in a crystalline form, and the crystalline form has XRPD 2-theta (2θ) peaks at 7.6°±0.2°, 10.3°±0.2°, 13.6°±0.2°, 19.2°±0.2°, 20.7°±0.2°, 33.4°±0.2°, and 38.2°±0.2°. In further embodiments, Compound 1 is in a crystalline form, and the crystalline form has XRPD 2-theta (2θ) peaks at 7.6°±0.2°, 10.3°±0.2°, 13.6°±0.2°, 19.2°±0.2°, 20.7°±0.2°, 30.1°±0.2°, 33.4°±0.2° and 38.2°±0.2°. In certain embodiments, Compound 1 is in a crystalline form, and the crystalline form has XRPD 2-theta (2θ) peaks at 7.6°±0.2°, 10.3°±0.2°, 13.6°±0.2°, 19.2°±0.2°, 20.7°±0.2°, 26.0°±0.2°, 30.1°±0.2°, 33.4°±0.2°, and 38.2°±0.2°. In still further embodiments, Compound 1 is in a crystalline form, and the crystalline form has at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty one, at least twenty two, or each of the XRPD 2-theta (2θ) peaks selected from the group consisting of 7.6°±0.2°, 10.3°±0.2°, 13.6°±0.2°, 14.8°±0.2°, 15.0°±0.2°, 15.4°±0.2°, 17.5°±0.2°, 18.3°±0.2°, 18.6°±0.2°, 19.2°±0.2°, 20.7°±0.2°, 21.3°±0.2°, 22.0°±0.2°, 23.6°±0.2°, 24.3°±0.2°, 25.2°±0.2°, 26.0°±0.2°, 27.2°±0.2°, 30.1°±0.2°, 32.4°±0.2°, 33.4°±0.2°, 38.2°±0.2°, and 39.4°±0.2°. In some embodiments, the crystalline form of Compound 1 has at least three of these peaks. In other embodiments, the crystalline form of Compound 1 has at least four of these peaks. In other embodiments, the crystalline form of Compound 1 has at least five of these peaks. In other embodiments, the crystalline form of Compound 1 has at least six of these peaks. In other embodiments, the crystalline form of Compound 1 has at least seven of these peaks. In other embodiments, the crystalline form of Compound 1 has at least eight of these peaks. In other embodiments, the crystalline form of Compound 1 has at least nine of these peaks. In other embodiments, the crystalline form of Compound 1 has at least ten of these peaks. In certain embodiments, for a crystalline form of Compound 1 with XRPD 2-theta (2θ) peaks at 7.6°±0.2° and 20.7°±0.2° (including, for example, a crystalline form with three, four, five, six, seven, eight or more XRPD peaks as described herein), the peak at 7.6°±0.2° has greater than 50% relative intensity, and the peak at 20.7°±0.2° has 100% relative intensity.

B. Bulk Compositions

In some embodiments, provided herein are bulk compositions comprising Compound 1.

Bulk compositions may include, for example, compositions comprising at least 1 kg of Compound 1, at least 10 kg of Compound 1, at least 50 kg of Compound 1, at least 100 kg of Compound 1, at least 150 kg of Compound 1, at least 200 kg of Compound 1, at least 250 kg of Compound 1, at least 300 kg of Compound 1, at least 350 kg of Compound 1, at least 400 kg of Compound 1, at least 450 kg of Compound 1, or at least 500 kg of Compound 1. In some embodiments, the bulk composition comprises between about 50 kg to about 500 kg of Compound 1, between about 100 kg to about 400 kg of Compound 1, between about 100 kg to about 300 kg of Compound 1, between about 150 kg to about 250 kg of Compound 1, between about 200 kg to about 350 kg of Compound 1, or between about 200 kg to about 300 kg of Compound 1.

In further embodiments, provided herein are bulk compositions comprising Compound 1 and at least one container. Any suitable container may be used. For example, in some embodiments, the container is a box, a bucket, a barrel, a bottle, a jar, a bag, a crate, a pail, a tray, or a tarp. In some embodiments, the bulk composition comprises Compound 1 and two or more containers, such as three containers, four containers, five containers, or greater than five containers. In bulk compositions comprising two or more containers, in some embodiments each of the two or more containers are the same type, for example they are each a barrel, each a pail, each a box, etc. In other embodiments of bulk compositions comprising two or more containers, at least two containers are of different types. In certain embodiments, the bulk composition comprises Compound 1 and at least one container, wherein each container is independently selected from the group consisting of a box, a bucket, a barrel, a bottle, a jar, a bag, a crate, a pail, a tray, and a tarp. In certain embodiments, the container comprises a lid, for example a screw-top lid or a lid that snaps on. In some embodiments, the lid is detachable, while in other embodiments it is attached, for example by a tether. The container may comprise any suitable material, or combination of materials. For example, in some embodiments the container comprises glass, metal, plastic, cardboard, wood, or any combinations thereof. In embodiments in which the bulk composition comprises two or more containers, in some embodiments each container comprises the same material, while in other embodiments at least two of the containers comprise different materials. In some embodiments, the one or more containers of the bulk composition are free of contaminants. For example, in some embodiments the one or more containers are suitable for use in storing an active pharmaceutical ingredient (API) intended for administration to a mammal, such as a human.

In some embodiments, at least a portion of the Compound 1 of the bulk composition is inside one or more containers. In certain embodiments, at least 10%, at least 20%, at least 30%, at least 40%, at least 50%, at least 60%, at least 70%, at least 80%, at least 90%, at least 95%, at least 99% of the bulk composition is located within one or more containers. In some embodiments, provided herein is a bulk composition comprising Compound 1 and two or more containers, wherein each container contains at least a portion of the Compound 1. In certain embodiments, at least 10%, at least 20%, at least 30%, at least 40%, at least 50%, at least 60%, at least 70%, at least 80%, at least 90%, at least 95%, at least 99% of Compound 1, in total, is located within the two or more containers. At least a portion of Compound 1 of the bulk composition may, in some embodiments, be evenly distributed between the two or more containers, or in other embodiments may be unevenly distributed.

In some embodiments, the bulk composition comprises at least 50% by weight, at least 55% by weight, at least 60% by weight, at least 65% by weight, at least 70% by weight, at least 75% by weight, at least 80% by weight, at least 85% by weight, at least 90% by weight, at least 95% by weight, at least 96% by weight, at least 97% by weight, at least 98% by weight, at least 99% by weight, or at least 99.9% by weight of Compound 1, wherein the weight % excludes the weight of the container. In certain embodiments, the bulk composition comprises at least 75% by weight of Compound 1, excluding the weight of the container.

In some embodiments, the bulk composition comprises less than about 6000 ppm of organic solvent. In some embodiments, the bulk composition comprises less than about 5500 ppm, less than about 5000 ppm, less than about 4500 ppm, less than about 4000 ppm, less than about 3500 ppm, less than about 3000 ppm, less than about 2500 ppm, or less than about 2000 ppm organic solvent. In some embodiments, the organic solvent comprises one or more alcohols. In some embodiments, the organic solvent comprises one or more $C_1$-$C_8$, or $C_1$-$C_6$, or $C_1$-$C_4$ alcohols. In certain embodiments, the organic solvent comprises isopropanol, n-propanol, ethanol, or methanol, or any combinations thereof. In some embodiments, the organic solvent comprises isopropanol.

C. Pharmaceutical Compositions, Dosage Forms, and Kits

Also provided herein are pharmaceutical compositions comprising Compound 1 and a pharmaceutically acceptable excipient. Pharmaceutically acceptable excipients may include, for example, an adjuvant, carrier, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

In some embodiments, the pharmaceutical composition is a solid. For example, in some embodiments, the pharmaceutical composition is a powder, or a tablet. In certain embodiments, the pharmaceutical composition is combined with a suitable medium to produce a liquid, and the liquid is administered to a subject in need thereof. In some embodiments, the liquid is administered parenterally (for example, intravenously). In other embodiments, the liquid is administered enterally, such as through a gastrointestinal tube (for example orally or rectally through a gastrointestinal tube). In some embodiments, the liquid is administered orally, such as with a syringe, cup, or spoon. In some embodiments, the suitable medium is aqueous.

Further provided herein are dosage forms comprising a pharmaceutical composition as described herein. In some embodiments, the dosage form comprises one or more tablets, or one or more capsules. In some embodiments, the dosage form is a powder in a sealed vial, which is combined with a suitable medium before being administered. In some embodiments, the suitable medium is aqueous.

In yet still further embodiments, provided herein are kits comprising a dosage form as described herein, and packaging. Any suitable packaging may be used. In some embodiments, the packaging comprises a bottle, or a blister pack, or a vial. In some embodiments, the kit comprises a dosage form, wherein the dosage form comprises one or more tablets or one or more capsules, and packaging, wherein the packaging is a blister pack. The blister pack, in some embodiments, is sealed with a plastic film, or a foil film, or a film comprising plastic and foil. In some embodiments, the kit comprises a suitable medium to be mixed with the dosage form prior to administration to the subject in need thereof. For example, in some embodiments the kit comprises a dosage form as a powder in a sealed vial, and an aqueous medium in a separate container (such as a vial, or syringe, or bottle), and the dosage form is combined with the aqueous medium before being administered to the subject in need thereof (for example, orally).

In some embodiments, the pharmaceutical composition, dosage form, or kit comprises less than about 6000 ppm of organic solvent. In some embodiments, the pharmaceutical composition, dosage form, or kit comprises less than about 5500 ppm, less than about 5000 ppm, less than about 4500 ppm, less than about 4000 ppm, less than about 3500 ppm, less than about 3000 ppm, less than about 2500 ppm, or less than about 2000 ppm organic solvent. In some embodiments, the organic solvent comprises one or more alcohols. In some embodiments, the organic solvent comprises one or more $C_1$-$C_8$, or $C_1$-$C_6$, or $C_1$-$C_4$ alcohols. In certain embodiments, the organic solvent comprises isopropanol, n-propanol, ethanol, or methanol, or any combinations thereof. In some embodiments, the organic solvent comprises isopropanol.

D. Water Content and Ratios

In certain embodiments, the bulk composition, pharmaceutical composition, dosage form, kit, or medicament comprises at least about 5.0%, at least about 5.5%, at least about 6.0%, at least about 6.5%, at least about 7.0%, at least about 7.5%, at least about 8.0%, at least about 8.5%, at least about 9.0%, at least about 9.5%, at least about 10.0%, at least about 10.5%, at least about 11.0%, at least about 11.5%, or at least about 12.0% by weight water relative to the total weight of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt present in anhydrous or trihydrate form. In some embodiments, the bulk composition, pharmaceutical composition, dosage form, kit, or medicament comprises between about 6.5% by weight to about 10% by weight, or between about 7.5% by weight to about 9.0% by weight, or about 8.5% by weight water, relative to the total weight of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt present in the trihydrate form, and (if present) the anhydrous form. In some embodiments, only the trihydrate form is present. In certain embodiments, the anhydrous form is also present, and the water content is evaluated relative to the total weight of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt in both the trihydrate and the anhydrous forms. In some embodiments, the bulk composition, pharmaceutical composition, dosage form, kit, or medicament comprises at least about 7.5% by weight water, relative to the total weight of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt present in the trihydrate form, and (if present) the anhydrous form. The water content of the bulk composition, pharmaceutical composition, dosage form, kit, or medicament includes the water present in the trihydrate form of the compound.

In some embodiments, the bulk composition, pharmaceutical composition, dosage form, kit, or medicament provided herein further comprises an anhydrous form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt. In certain embodiments, the ratio of Compound 1 to the anhydrous form is at least about 2 to 1, at least about 3 to 1, at least about 4 to 1, at least about 5 to 1, at least about 6 to 1, at least about 7 to 1, at least about 8 to 1, at least about 9 to 1, at least about 10 to 1, at least about 11 to 1, or at least about 12 to 1. In some embodiments, the bulk composition, pharmaceutical composition, dosage form, kit, or medicament comprises an anhydrous form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt, and the ratio of Compound 1 to the anhydrous form is at least 4 to 1, or at least 11 to 1.

E. Stability

In some embodiments, the bulk compositions, pharmaceutical compositions, dosage forms, medicaments, or kits comprising Compound 1 provided herein have increased stability relative to bulk compositions, pharmaceutical compositions, dosage forms, medicaments, or kits comprising the anhydrous form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt. For example, in some embodiments, the bulk compositions, pharmaceutical compositions, dosage forms, medicaments, or kits comprising Compound 1 provided herein have a more stable weight over time compared to bulk compositions, pharmaceutical compositions, dosage forms, medicaments, or kits comprising the anhydrous compound. In certain embodiments, the bulk compositions, pharmaceutical compositions, dosage forms, medicaments, or kits comprising Compound 1 provided herein have less than 10%, less than 9%, less than 8%, less than 7%, less than 6%, less than 5%, less than 4%, less than 3%, less than 2.5%, less than 2%, less than 1.5%, less than 1%, or less than 0.5% change in mass over at least 3 months, at least 6 months, at least 9 months, at least 12 months, at least 15 months, at least 18 months, at least 24 months, at least 30 months, at least 36 months, at least 42 months, or at least 48 months. In some embodiments, the change in mass is an increase in mass. In some embodiments, the change in mass is a decrease in mass. In some embodiments, the bulk compositions, pharmaceutical compositions, dosage forms, medicaments, or kits comprising Compound 1 are more stable in certain conditions than bulk compositions, pharmaceutical compositions, dosage forms, medicaments, or kits comprising the anhydrous compound. For example, in some embodiments, the environment has a relative humidity of greater than 10%, greater than 20%, greater than 30%, greater than 40%, greater than 50%, greater than 60%, greater than 70%, greater than 80%, greater than 90%, 10% or greater, 20% or greater, 30% or greater, 40% or greater, 50% or greater, 60% or greater, 70% or greater, 80% or greater, or about 60%. In some embodiments, the temperature is between 15° C. and 35° C. or between 20° C. and 30° C. In certain embodiments, the temperature is about 25° C. In other embodiments, the temperature is less than 35° C., less than 30° C., greater than 10° C., greater than 15° C., or greater than 20° C. In certain embodiments, the bulk compositions, pharmaceutical compositions, dosage forms, medicaments, or kits comprising Compound 1 provided herein have less than 8%, less than 4%, or less than 2% change in mass (such as increase in mass) over at least 3 months, at least 6 months, at least 9 months, at least 12 months, at least 18 months, at least 24 months, or at least 36 months when stored in an environment between 15° C. and 35° C. (such as between 20° C. and 30° C., or about 25° C.) and a relative humidity of greater than 30% (such as greater than 50%, or about 60%).

II. Methods of Using Compound 1

Further provided herein are methods of treating a disorder in a subject in need thereof, comprising administering to the subject in need thereof a therapeutically effective amount of Compound 1 In some embodiments, a pharmaceutical composition comprising Compound 1 and a pharmaceutically acceptable excipient is administered to the subject. Further provided herein are methods of improving gastrointestinal motility in a subject in need thereof, comprising administering to the subject in need thereof a therapeutically effective amount of Compound 1, or administering a pharmaceutical composition comprising Compound 1 and a pharmaceutically acceptable excipient. In addition, provided herein is the use of Compound 1, or a pharmaceutical composition comprising Compound 1, in treating a disorder in a subject in need thereof or for improving gastrointestinal motility in a subject in need thereof, and use of Compound 1 in the manufacture of a medicament for treating a disorder in a subject in need thereof or for improving gastrointestinal motility in a subject in need thereof.

In some embodiments of treating a disorder in a subject in need thereof (such as methods, use of Compound 1, use of a pharmaceutical composition comprising Compound 1, or use of Compound 1 in the manufacture of a medicament), the disorder is a gastrointestinal disorder. In some embodiments of improving gastrointestinal motility in a subject in need thereof (such as methods, use of Compound 1, use a pharmaceutical composition comprising Compound 1, or use of Compound 1 in the manufacture of a medicament), the subject in need thereof has a gastrointestinal disorder. In certain embodiments, the gastrointestinal disorder is gastroesophageal reflux disease (GERD), dyspepsia (such as functional dyspepsia or functional motility disorder), gastroparesis, paralytic ileus, post-operative ileus, emesis, nausea, heartburn, intestinal pseudo-obstruction, irritable bowel syndrome (IBS), constipation, enteral feeding intolerance (EFI), esophagitis, chronic grass sickness, megacolon, gastritis, gastrointestinal stasis, or abomasal emptying defect.

In some embodiments, the subject in need thereof is a human. In certain embodiments, wherein the subject in need thereof is a human, the gastrointestinal disorder is gastroesophageal reflux disease (GERD), dyspepsia (such as functional dyspepsia or functional motility disorder), gastroparesis, paralytic ileus, post-operative ileus, emesis, nausea, heartburn, intestinal pseudo-obstruction, irritable bowel syndrome (IBS), constipation, enteral feeding intolerance (EFI), or esophagitisis. In other embodiments, the subject in need thereof is a non-human mammal, such as a ruminant (e.g., sheep, cow, yak, bison, or buffalo), an equine (e.g., a horse (including a pony) or donkey), a cat, a dog, a rabbit, or a guinea pig. In some embodiments, wherein the subject in need therein is a non-human mammal, the gastrointestinal disorder is post-operative ileus, chronic grass sickness, constipation, megacolon, gastritis, gastrointestinal stasis, or abomasal emptying defect.

In some embodiments, provided herein is a method of treating gastroesophageal reflux disease (GERD) in a subject in need thereof comprising administering to the subject in need thereof a therapeutically effective amount of Compound 1, or administering to the subject in need thereof a pharmaceutical composition comprising a therapeutically effective amount of Compound 1 and a pharmaceutically acceptable excipient. In some embodiments, provided herein is Compound 1, or a pharmaceutical composition comprising Compound 1, for use in treating GERD, or use of Compound 1 in manufacturing a medicament for treating GERD. In some embodiments of methods of treatment, Compound 1 for use in, or a pharmaceutical composition comprising Compound 1 for use in, or use of Compound in manufacturing a medicament for improving gastrointestinal motility in a subject in need thereof, the subject in need thereof has a gastrointestinal disorder, wherein the gastrointestinal disorder is GERD. GERD is a disease characterized as the backward flow of the stomach contents into the esophagus. One important factor in the pathogenesis of gastroesophageal reflux disease is a reduction in the pressure barrier due to the failure of the lower esophageal sphincter. Failure of the lower esophageal sphincter can arise due to a low basal pressure, sphincter relaxation, or to a non-compensated increase in intragastric pressure. Other factors in the pathogenesis of the disease may include delayed gastric emptying, insufficient esophageal clearing due to impaired peristalsis, or the corrosive nature of the reflux material, which can damage esophageal mucosa. In some embodiments, the GERD is proton pump inhibitor (PPI) resistant GERD. PPI resistant GERD may include, for example, GERD in subjects that which does not improve with administration of a PPI, or in which the main complaint of the subject has improved less than 50% with administration of a PPI. Thus, in some embodiments, provided herein is a method of treating; Compound 1 for use in treating; a pharmaceutical composition comprising Compound 1 for use in treating; or use of Compound 1 in manufacturing a medicament for treating GERD, wherein the GERD is PPI-resistant GERD. In some embodiments, the subject in need thereof is human.

In some embodiments, provided herein is a method of treating dyspepsia in a subject in need thereof comprising administering to the subject in need thereof a therapeutically effective amount of Compound 1, or administering to the subject in need thereof a pharmaceutical composition comprising a therapeutically effective amount of Compound 1 and a pharmaceutically acceptable excipient. In some embodiments, provided herein is Compound 1, or a pharmaceutical composition comprising Compound 1, for use in treating dyspepsia, or use of Compound 1 in manufacturing a medicament for treating dyspepsia. In some embodiments of methods of treatment, Compound 1 for use in, a pharmaceutical composition comprising Compound 1 for use in, or use of Compound in manufacturing a medicament for improving gastrointestinal motility in a subject in need thereof, the subject in need thereof has a gastrointestinal disorder, wherein the gastrointestinal disorder is dyspepsia. Dyspepsia is a condition characterized by an impairment of the power or function of digestion, and can arise as a symptom of a primary gastrointestinal dysfunction or as a complication of other disorders, such as appendicitis, gallbladder disorders, or malnutrition. Thus, in some embodiments, treating dyspepsia comprises treating dyspepsia associated with appendicitis, treating dyspepsia associated with a gallbladder disorder, or treating dyspepsia associated with malnutrition, or treating functional dyspepsia (FD), or treating all of these. In some embodiments, treating dyspepsia is treating functional dyspepsia (FD). Functional dyspepsia may also be called functional motility disorder (FMD). In some embodiments, the subject in need thereof is human. In other embodiments, the subject in need thereof is a non-human animal, such as a ruminant (such as a sheep, cow, yak, bison, or buffalo), or an equine (such as a horse (which may include a pony) or donkey), a cat, a dog, a rabbit, or a guinea pig.

In some embodiments, provided herein is a method of treating gastroparesis in a subject in need thereof, comprising administering to the subject in need thereof a therapeutically effective amount of Compound 1, or administering to the subject in need thereof a pharmaceutical composition comprising a therapeutically effective amount of Compound 1 and a pharmaceutically acceptable excipient. In some embodiments, provided herein is Compound 1, or a pharmaceutical composition comprising Compound 1, for use in treating gastroparesis, or use of Compound 1 in manufacturing a medicament for treating gastroparesis. In some embodiments of methods of treatment, Compound 1 for use in, a pharmaceutical composition comprising Compound 1 for use in, or use of Compound in manufacturing a medicament for improving gastrointestinal motility in a subject in need thereof, the subject in need thereof has a gastrointestinal disorder, wherein the gastrointestinal disorder is gastroparesis. Gastroparesis is a paralysis of the stomach brought about by a motor abnormality in the stomach, and can be a complication of a disease such as diabetes, progressive systemic sclerosis, anorexia nervosa, or myotonic dystrophy. In some embodiments, treating gastroparesis comprises treating diabetic gastroparesis, treating gastroparesis associated with progressive systemic sclerosis, treating gastroparesis associated with anorexia nervosa, or treating gastroparesis associated with myotonic dystrophy, or treating any combination of these. In some embodiments, the gastroparesis is idiopathic gastroparesis, or functional gastroparesis. In some embodiments, the subject in need thereof is human.

In some embodiments, provided herein is a method of treating paralytic ileus in a subject in need thereof, comprising administering to the subject in need thereof a therapeutically effective amount of Compound 1, or administering to the subject in need thereof a pharmaceutical composition comprising a therapeutically effective amount of Compound 1 and a pharmaceutically acceptable excipient. In some embodiments, provided herein is Compound 1, or a pharmaceutical composition comprising Compound 1, for use in treating paralytic ileus, or use of Compound 1 in manufacturing a medicament for treating paralytic ileus. In some embodiments of methods of treatment, Compound 1 for use in, a pharmaceutical composition comprising Compound 1 for use in, or use of Compound in manufacturing a medicament for improving gastrointestinal motility in a subject in need thereof, the subject in need thereof has a gastrointestinal disorder, wherein the gastrointestinal disorder is paralytic ileus. In some embodiments, the subject in need thereof is human.

In some embodiments, provided herein is a method of treating post-operative ileus in a subject in need thereof, comprising administering to the subject in need thereof a therapeutically effective amount of Compound 1, or administering to the subject in need thereof a pharmaceutical composition comprising a therapeutically effective amount of Compound 1 and a pharmaceutically acceptable excipient. In some embodiments, provided herein is Compound 1, or a pharmaceutical composition comprising Compound 1, for use in treating post-operative ileus, or use of Compound 1 in manufacturing a medicament for treating post-operative ileus. In some embodiments of methods of treatment, Compound 1 for use in, a pharmaceutical composition comprising Compound 1 for use in, or use of Compound in manufacturing a medicament for improving gastrointestinal motility in a subject in need thereof, the subject in need thereof has a gastrointestinal disorder, wherein the gastrointestinal disorder is post-operative ileus. Post-operative ileus is an obstruction in the intestine due to a disruption in muscle tone following surgery. In some embodiments of treating post-operative ileus, the subject in need thereof is a human. In other embodiments, the subject in need thereof is a non-human animal, such as an equine animal, for example a horse (which may include a pony).

In some embodiments, provided herein is a method of treating nausea or emesis in a subject in need thereof, comprising administering to the subject in need thereof a therapeutically effective amount of Compound 1, or administering to the subject in need thereof a pharmaceutical composition comprising a therapeutically effective amount of Compound 1 and a pharmaceutically acceptable excipient. In some embodiments, provided herein is Compound 1, or a pharmaceutical composition comprising Compound 1, for use in treating nausea, or use in treating emesis, or use of Compound 1 in manufacturing a medicament for treating nausea, or for treating emesis. In some embodiments of methods of treatment, Compound 1 for use in, a pharmaceutical composition comprising Compound 1 for use in, or use of Compound in manufacturing a medicament for improving gastrointestinal motility in a subject in need thereof, the subject in need thereof has a gastrointestinal disorder, wherein the gastrointestinal disorder is nausea. In other embodiments, the gastrointestinal disorder is emesis. In some embodiments, the subject in need thereof is human.

In some embodiments, provided herein is a method of treating heartburn in a subject in need thereof, comprising administering to the subject in need thereof a therapeutically effective amount of Compound 1, or administering to the subject in need thereof a pharmaceutical composition comprising a therapeutically effective amount of Compound 1 and a pharmaceutically acceptable excipient. In some embodiments, provided herein is Compound 1, or a pharmaceutical composition comprising Compound 1, for use in treating heartburn, or use of Compound 1 in manufacturing a medicament for treating heartburn. In some embodiments of methods of treatment, Compound 1 for use in, a pharmaceutical composition comprising Compound 1 for use in, or use of Compound in manufacturing a medicament for improving gastrointestinal motility in a subject in need thereof, the subject in need thereof has a gastrointestinal disorder, wherein the gastrointestinal disorder is heartburn. In some embodiments, the subject in need thereof is human.

In some embodiments, provided herein is a method of treating intestinal pseudo-obstruction in a subject in need thereof, comprising administering to the subject in need thereof a therapeutically effective amount of Compound 1, or administering to the subject in need thereof a pharmaceutical composition comprising a therapeutically effective amount of Compound 1 and a pharmaceutically acceptable excipient. In some embodiments, provided herein is Compound 1, or a pharmaceutical composition comprising Compound 1, for use in treating intestinal pseudo-obstruction, or use of Compound 1 in manufacturing a medicament for treating intestinal pseudo-obstruction. In some embodiments of methods of treatment, Compound 1 for use in, a pharmaceutical composition comprising Compound 1 for use in, or use of Compound in manufacturing a medicament for improving gastrointestinal motility in a subject in need thereof, the subject in need thereof has a gastrointestinal disorder, wherein the gastrointestinal disorder is intestinal pseudo-obstruction. Intestinal pseudo-obstruction is a condition characterized by constipation, colicky pain, and vomiting, but without evidence of physical obstruction. In some embodiments, treating intestinal pseudo-obstruction comprises treating constipation associated with intestinal pseudo-obstruction, treating colicky pain associated with intestinal pseudo-obstruction, or treating vomiting associated with intestinal pseudo-obstruction, or treating all of these. In some embodiments, the subject in need thereof is human.

In some embodiments, provided herein is a method of treating irritable bowel syndrome (IBS) in a subject in need thereof, comprising administering to the subject in need thereof a therapeutically effective amount of Compound 1, or administering to the subject in need thereof a pharmaceutical composition comprising a therapeutically effective amount of Compound 1 and a pharmaceutically acceptable excipient. In some embodiments, provided herein is Compound 1, or a pharmaceutical composition comprising Compound 1, for use in treating IBS, or use of Compound 1 in manufacturing a medicament for treating IBS. In some embodiments of methods of treatment, Compound 1 for use in, a pharmaceutical composition comprising Compound 1 for use in, or use of Compound in manufacturing a medicament for improving gastrointestinal motility in a subject in need thereof, the subject in need thereof has a gastrointestinal disorder, wherein the gastrointestinal disorder is IBS. IBS is a condition that is characterized by abdominal pain due to abnormal colon contractions, and is often associated with constipation and diarrhea. Thus, in some embodiments, treating IBS comprises treating abdominal pain associated with IBS, or treating constipation associated with IBS, or treating diarrhea with IBS. In some embodiments, the IBS is irritable bowel syndrome constipation type (IBSc). In some embodiments, the subject in need thereof is human.

In some embodiments, provided herein is a method of treating constipation in a subject in need thereof, comprising administering to the subject in need thereof a therapeutically effective amount of Compound 1, or administering to the subject in need thereof a pharmaceutical composition comprising a therapeutically effective amount of Compound 1 and a pharmaceutically acceptable excipient. In some embodiments, provided herein is Compound 1, or a pharmaceutical composition comprising Compound 1, for use in treating constipation, or use of Compound 1 in manufacturing a medicament for treating constipation. In some embodiments of methods of treatment, Compound 1, or a pharmaceutical composition comprising Compound 1, for use in, or use of Compound in manufacturing a medicament for improving gastrointestinal motility in a subject in need thereof, the subject in need thereof has a gastrointestinal disorder, wherein the gastrointestinal disorder is constipation. Constipation is a condition characterized by infrequent or difficult evacuation of feces, and may result from a condition such as lack of intestinal muscle tone or intestinal spasticity. Thus, in some embodiments, treating constipation comprises treating constipation associated with low intestinal muscle tone, treating constipation associated with intestinal spasticity, treating constipation associated with IBS, treating constipation associated with intestinal pseudo-obstruction, treating opiate-induced constipation (OIC), treating chronic idiopathic constipation (CIC), or treating constipation associated with irritable bowel constipation type (IBSc). In some embodiments, the constipation is chronic constipation. In some embodiments, the subject in need thereof is a human. In other embodiments, the subject in need thereof is a non-human mammal, such as a cat, or a dog.

In some embodiments, provided herein is a method of treating enteral feeding intolerance (EFI) in a subject in need thereof, comprising administering to the subject in need thereof a therapeutically effective amount of Compound 1, or administering to the subject in need thereof a pharmaceutical composition comprising a therapeutically effective amount of Compound 1 and a pharmaceutically acceptable excipient. In some embodiments, provided herein is Compound 1, or a pharmaceutical composition comprising Compound 1, for use in treating EFI, or use of Compound 1 in manufacturing a medicament for treating EFI. In some embodiments of methods of treatment, Compound 1 for use in, a pharmaceutical composition comprising Compound 1 for use in, or use of Compound in manufacturing a medicament for improving gastrointestinal motility in a subject in need thereof, the subject in need thereof has a gastrointestinal disorder, wherein the gastrointestinal disorder is EFI. EFI in critical-illness patients is common. It is often characterized by one or more of vomiting, abdominal distention, complaints of discomfort, high nasogastric tube output, high gastric residual volumes (GRVs) measured at intervals, diarrhea, reduced passage of flatus and stool, or abnormal abdominal radiographs. Critical-illness patients suffering from EFI are associated with a longer stay in ICU and reduced survival. In some embodiments, treating EFI comprises one or more of treating vomiting associated with EFI, treating abdominal distention associated with EFI, treating discomfort associated with EFI, treating high nasogastric tube output associated with EFI, treating high gastric residual volumes (GRVs) associated with EFI, treating diarrhea associated with EFI, or treating reduced passage of flatus and stool associated with EFI. In some embodiments, the subject in need thereof is human.

In still further embodiments, provided herein is a method of treating esophagitis in a subject in need thereof, comprising administering to the subject in need thereof a therapeutically effective amount of Compound 1, or administering to the subject in need thereof a pharmaceutical composition comprising a therapeutically effective amount of Compound 1 and a pharmaceutically acceptable excipient. In some embodiments, provided herein is Compound 1, or a pharmaceutical composition comprising Compound 1, for use in treating esophagitis, or use of Compound 1 in manufacturing a medicament for treating esophagitis. In some embodiments of methods of treatment, Compound 1 for use in, a pharmaceutical composition comprising Compound 1 for use in, or use of Compound in manufacturing a medicament for improving gastrointestinal motility in a subject in need thereof, the subject in need thereof has a gastrointestinal disorder, wherein the gastrointestinal disorder is esophagitis. Esophagitis includes inflammation of the lining of the esophagus, and nay be caused by, for example backflow of acid from the stomach into the esophagus (for example, in GERD), or allergic inflammation of the esophageal tissue. In some embodiments, the esophagitis is erosive esophagitis (EE) or eosinophilic esophagitis (EoE). Thus, in some embodiments treating esophagitis includes treating erosive esophagitis or eosinophilic esophagitis. In some embodiments, the subject in need thereof is human.

In further embodiments, provided herein is a method of treating chronic grass sickness in a subject in need thereof, comprising administering to the subject in need thereof a therapeutically effective amount of Compound 1, or a pharmaceutical composition comprising a therapeutically effective amount of Compound 1 and a pharmaceutically acceptable excipient. In some embodiments, provided herein is Compound 1, or a pharmaceutical composition comprising Compound 1, for use in treating chronic grass sickness, or use of Compound 1 in manufacturing a medicament for treating chronic grass sickness in a subject in need thereof. In some embodiments of methods of treatment, Compound 1 for use in, a pharmaceutical composition comprising Compound 1 for use in, or use of Compound in manufacturing a medicament for improving gastrointestinal motility in a subject in need thereof, the subject in need thereof has a gastrointestinal disorder, wherein the gastrointestinal disorder is chronic grass sickness. In some embodiments of the methods of treatment, Compound 1 for use in, a pharmaceutical composition comprising Compound 1 for use in, or use of Compound in manufacturing a medicament for treating chronic grass sickness in a subject in need thereof, the subject in need thereof is a non-human animal, such as an equine or a ruminant. In some embodiments, the equine is a horse (which may be a pony) or a donkey. In some embodiments, the ruminant is a sheep. Chronic grass sickness includes impaired activity of the gut due to damage to the autonomic (involuntary) nervous system, and is a form of autonomic dystonia. Chronic grass sickness in an equine may also be known as equine dysautonomia.

In other embodiments, provided herein is a method of treating megacolon in a subject in need thereof, comprising administering to the subject in need thereof a therapeutically effective amount of Compound 1, or a pharmaceutical composition comprising a therapeutically effective amount of Compound 1 and a pharmaceutically acceptable excipient. In some embodiments, provided herein is Compound 1, or a pharmaceutical composition comprising Compound 1, for use in treating megacolon, or use of Compound 1 in manufacturing a medicament for treating megacolon. In some embodiments of methods of treatment, Compound 1 for use in, a pharmaceutical composition comprising Compound 1 for use in, or use of Compound in manufacturing a medicament for improving gastrointestinal motility in a subject in need thereof, the subject in need thereof has a gastrointestinal disorder, wherein the gastrointestinal disorder is megacolon. In some embodiments of methods of treatment, Compound 1 for use in, a pharmaceutical composition comprising Compound 1 for use in, or use of Compound in manufacturing a medicament for treating megacolon in a subject in need thereof, the subject in need thereof is a non-human animal, such as a companion animal. In certain embodiments, the subject in need thereof is a cat or a dog. Megacolon includes an abnormal dilation of the colon (also called the large intestine), and is often accompanied by a paralysis of the peristaltic movements of the bowel.

In still further embodiments, provided herein is a method of treating gastritis in a subject in need thereof, comprising administering to the subject in need thereof a therapeutically effective amount of Compound 1, or a pharmaceutical composition comprising a therapeutically effective amount of Compound 1 and a pharmaceutically acceptable excipient. In some embodiments, provided herein is Compound 1, or a pharmaceutical composition comprising Compound 1, for use in treating gastritis, or use of Compound 1 in manufacturing a medicament for treating gastritis. In some embodiments of methods of treatment, Compound 1 for use in, a pharmaceutical composition comprising Compound 1 for use in, or use of Compound in manufacturing a medicament for improving gastrointestinal motility in a subject in need thereof, the subject in need thereof has a gastrointestinal disorder, wherein the gastrointestinal disorder is gastritis. In some embodiments of methods of treatment, Compound 1 for use in, a pharmaceutical composition comprising Compound 1 for use in, or use of Compound in manufacturing a medicament for treating gastritis in a subject in need thereof, the subject in need thereof is a non-human animal, such as a companion animal. In certain embodiments, the subject in need thereof is a cat. In certain embodiments, the gastritis is atrophic gastritis. Gastritis is an inflammation of the gastric mucosa, and symptoms may include acute vomiting, decreased appetite, dehydration, lethargy or depression, increased thirst, blood in the vomit or feces, and abdominal pain.

In certain embodiments, provided herein is a method of treating gastrointestinal stasis in a subject in need thereof, comprising administering to the subject in need thereof a therapeutically effective amount of Compound 1, or a pharmaceutical composition comprising a therapeutically effective amount of Compound 1 and a pharmaceutically acceptable excipient. In some embodiments, provided herein is Compound 1, or a pharmaceutical composition comprising Compound 1, for use in treating gastrointestinal stasis, or use of Compound 1 in manufacturing a medicament for treating gastrointestinal stasis in a subject in need thereof. In some embodiments of methods of treatment, Compound 1 for use in, a pharmaceutical composition comprising Compound 1 for use in, or use of Compound in manufacturing a medicament for treating gastrointestinal stasis, the subject in need thereof is a rabbit or a guinea pig. Gastrointestinal stasis is the slowdown or complete cessation of gastrointestinal movement. In, for example, rabbits or guinea pigs, the intestine can become static for a variety of reasons, which may include stress, dehydration, pain from another underlying disorder or illness (such as gas, dental problems, infections, or urinary tract disorders), an intestinal blockage, or insufficient dietary crude fiber. Left untreated, the slowdown or complete cessation of normal intestinal movement (peristalsis) can result in death.

In other embodiments, provided herein is a method of treating abomasal emptying defect in a subject in need thereof, comprising administering to the subject in need thereof a therapeutically effective amount of Compound 1, or a pharmaceutical composition comprising a therapeutically effective amount of Compound 1 and a pharmaceutically acceptable excipient. In some embodiments, provided herein is Compound 1, or a pharmaceutical composition comprising Compound 1, for use in treating abomasal emptying defect, or use of Compound 1 in manufacturing a medicament for treating abomasal emptying defect. In some embodiments of methods of treatment, Compound 1 for use in, a pharmaceutical composition comprising Compound 1 for use in, or use of Compound in manufacturing a medicament for improving gastrointestinal motility in a subject in need thereof, the subject in need thereof has a gastrointestinal disorder, wherein the gastrointestinal disorder is abomasal emptying defect. In some embodiments of methods of treatment, Compound 1 for use in, a pharmaceutical composition comprising Compound 1 for use in, or use of Compound in manufacturing a medicament for treating abomasal emptying defect in a subject in need thereof, the subject in need thereof is a non-human animal, such as a ruminant, for example a domesticated ruminant. In some embodiments, the ruminant is a sheep, cow (which may include a bull), yak, bison, or buffalo. Abomasal emptying defect is the slowdown or complete cessation of abomasum emptying, characterized by distension and impaction of the abomasum.

In some embodiments, provided herein is a method of increasing the transfer of passive immunity to a colostrum-fed calf, comprising administering to the calf an effective amount of Compound 1, or a pharmaceutical composition comprising an effective amount of Compound 1 and a pharmaceutically acceptable excipient. In some embodiments, provided herein is Compound 1, or a pharmaceutical composition comprising Compound 1, for use in increasing the transfer of passive immunity to a colostrum-fed calf, or use of Compound 1 in manufacturing a medicament for increasing the transfer of passive immunity to a colostrum-fed calf. In some embodiments, the colostrum-fed calf is a colostrum-fed dairy calf. Neonatal calves must ingest colostrum during the first 24 hours after birth to acquire passive immunity via the active uptake of maternal IgG (maternal antibodies) across small intestinal epithelial cells. The mass of IgG absorbed from the small intestine of the colostrum-fed calf may depend, in part, on the rate of abomasal emptying (rate of emptying of the abomasum, the fourth chamber of the ruminants' stomach). The rate of abomasal emptying may influence the rate at which colostral IgG is delivered to the site of IgG absorption in the small intestine. An increased rate of abomasal emptying may, in some embodiments, result in an increased apparent efficiency of absorption because colostral IgG may reach the site of absorption in the small intestine earlier and at a higher luminal concentration.

As described herein, provided are methods of treatment, Compound 1 for use in, or a pharmaceutical composition comprising Compound 1 for use in, or use of Compound in manufacturing a medicament for improving gastrointestinal motility in a subject in need thereof. Poor gastrointestinal motility can include poor motility of the stomach, poor motility of the small intestine, poor motility of the large intestine, or poor motility of the pelvic floor, or combinations thereof. In some embodiments, poor gastrointestinal motility includes complete cessation of motility. Symptoms associated with poor gastrointestinal motility may include, for example, constipation, vomiting, bloating, diarrhea, or nausea. In some embodiments, poor gastrointestinal motility is associated with a gastrointestinal disorder, such as one of the gastrointestinal disorders described herein. In certain embodiments, improving gastrointestinal motility as described herein comprises improving gastric motility, or improving intestinal motility, or a combination thereof. In certain embodiments, improving intestinal motility comprises improving the motility of the small intestine, or improving the motility of the large intestine, or a combination thereof. In some embodiments, improving gastrointestinal motility includes increasing gastrointestinal smooth muscle activity from the esophagus through the proximal small bowel. In certain embodiments, this accelerates esophageal and small intestinal transit, and may also facilitate gastric emptying and increase lower esophageal sphincter tone. In some embodiments, improving gastrointestinal motility comprises treating functional motility disorder. Thus, in some embodiments, provided herein are methods of treatment, Compound 1 for use in, or a pharmaceutical composition comprising Compound 1 for use in, or use of Compound in manufacturing a medicament for treating functional motility disorder (FMD). Functional motility disorder may also be called functional dyspepsia (FD). In some embodiments of improving gastrointestinal motility, the subject in need thereof is a human. In other embodiments, the subject in need thereof is a non-human animal, such as a ruminant (such as a sheep, cow, yak, bison, or buffalo), or an equine (such as a horse (which may include a pony) or donkey), a cat, a dog, a rabbit, or a guinea pig.

In some embodiments of the methods and uses provided herein, the subject is a newborn. In some embodiments, the newborn is a newborn human. In other embodiments, the newborn is a bovine newborn, such as a colostrum-fed calf. In some embodiments, Compound 1 or a pharmaceutical composition comprising Compound 1 and a pharmaceutically acceptable excipient is administered to the subject parenterally (such as intravenously). In some embodiments, it is administered subcutaneously. In other embodiments, it is administered intramuscularly. In still further embodiments, it is administered intraperitoneally. In some embodiments, it is administered rectally. In certain embodiments, it is administered orally. In other embodiments, it is administered through a gastric tube. For example, in some embodiments a solid form of Compound 1 (such as a powder, or tablets), or a solid pharmaceutical compositions comprising Compound 1 (such as a powder or tablet compositions comprising Compound 1) is dissolved in suitable medium to form a liquid, and the liquid administered parenterally (such as intravenously), or orally, or by a gastric tube. In certain embodiments, a solid form of Compound 1, or a solid pharmaceutical composition comprising Compound 1, is administered orally to a subject in need thereof (e.g., as a powder, one or more tablets, or one or more capsules). In some embodiments, the Compound 1 administered to a subject in need thereof as described herein (such as in a pharmaceutical composition), or used in the manufacture of a medicament as described herein, has one or more of the properties described herein, for example a crystalline form with one or more XRPD peaks as described herein.

In certain embodiments of any of the methods and uses provided herein (including, for example, methods of treating, Compound 1 for use, a pharmaceutical composition comprising Compound 1 for use, or uses of Compound 1 in manufacturing a medicament) for treating disorders described herein, or for improving gastrointestinal motility as described herein, in a subject in need thereof, the subject in need thereof is an animal. In some embodiments, the animal is a mammal. In certain embodiments, the animal is a human. In other embodiments, the animal is a non-human animal. In certain embodiments, the animal is a ruminant, such as a domesticated ruminant. In some embodiments, the ruminant is a sheep, cow (which may include a bull), yak, bison, or buffalo. In other embodiments, the mammal is an equine, such as a domesticated equine. In certain embodiments, the equine is a horse (including a pony) or a donkey. In other embodiments, the animal is a cat, a dog, a rabbit, or a guinea pig. In certain embodiments, the animal is a companion animal, for example a pet horse, a pet donkey, a pet cat, a pet dog, a pet rabbit, or a pet guinea pig. In other embodiments, the animal is an animal used for food production, such as a sheep, cow, bison, buffalo, or yak. Thus, provided herein are methods of, Compound 1 for use in, a pharmaceutical composition comprising Compound 1 for use, or uses of Compound 1 in manufacturing a medicament for, treating the disorders described herein, or for improving gastrointestinal motility as described herein, in a human. In another aspect, provided herein are methods of, Compound 1 for use in, a pharmaceutical composition comprising Compound 1 for use, or uses of Compound 1 in manufacturing a medicament for, treating the disorders described herein, or for improving gastrointestinal motility as described herein, in a non-human mammal.

As described herein, provided are bulk compositions, pharmaceutical compositions, kits, and dosage forms comprising Compound 1 that have particular stability, or organic solvent content, or water content, or ratios of trihydrate to anhydrous form, or XRPD spectra, or various combinations of these. Any of these pharmaceutical compositions, dosage forms, or kits may, in some embodiments, be used in the methods and uses described herein for treating a disorder, or promoting gastrointestinal motility, in a subject in need thereof as provided herein. In some embodiments, any of these bulk compositions may be used in the methods and uses described herein for treating a disorder, or promoting gastrointestinal motility, in a subject in need thereof as provided herein, or may be used in the manufacture of a pharmaceutical formulation or dosage form or kit for use in the methods and uses described herein for treating a disorder, or promoting gastrointestinal motility, in a subject in need thereof as provided herein.

III. Methods of Producing Compound 1

In some aspects, provided herein are methods of producing Compound 1, and bulk compositions comprising Compound 1. In developing methods to produce bulk compositions of Compound 1, it has been surprisingly found that merely drying a wet mixture of di-hydrochloride salt of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester is does not always reliably produce a composition comprising Compound 1 with low (non-water) residual solvent. Rather, a stepped procedure of different temperatures and pressure ranges is, in some embodiments, a key aspect of the procedure to produce compositions comprising Compound 1 on a large scale. Furthermore, it has been found that there are at least three crystalline forms of the anhydrous di-hydrochloride salt of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester, and at least one crystalline form of Compound 1 (the trihydrate), and under certain conditions of solvent and temperature certain of these forms can interchange. The methods of making Compound 1 described herein may reproducibly yield Compound 1 with low (non-water) residual solvent and may be suitable for both laboratory scale and commercial scale manufacturing. The methods of making Compound 1 may also yield a crystalline form that has good handling properties, for example, low clumping and/or flows well.

In some embodiments, the method of making Compound 1 (such as methods of making a bulk composition comprising Compound 1) comprises:
(a) combining the free base (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester with organic solvent to form a mixture;
(b) adjusting the pH of the mixture to between 3.5 and 4.5 by the addition of hydrochloric acid;
(c) stirring the mixture until a precipitate is formed;
(d) isolating the precipitate to form an isolated precipitate; and
(e) drying the isolated precipitate under reduced pressure to produce the trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt (Compound 1).

Any suitable organic solvent may be combined with the free base to form the mixture. In some embodiments, the organic solvent comprises one or more compounds, such as one or more organic compounds, or at least one organic compound and one or more non-organic compounds. In certain embodiments, the organic solvent comprises one or more alcohols. In some embodiments, the organic solvent comprises one or more $C_1$-$C_8$, or $C_1$-$C_6$, or $C_1$-$C_4$ alcohols. In certain embodiments, the organic solvent comprises one or more of methanol, ethanol, n-propanol, or isopropanol. In some embodiments, the organic solvent comprises isopropanol. In some embodiments, the organic solvent comprises ethanol and n-propanol. In still further embodiments, the organic solvent comprises at least one organic compound and one or more non-organic compounds.

In certain embodiments, the free base is combined with organic solvent and water to form the mixture. For example, in some embodiments, the free base is combined with water and organic solvent to form the mixture, wherein the organic solvent comprises one or more alcohols, such as isopropanol. In some embodiments, the mixture may comprise, for example, various amounts of water. In certain embodiments, the mixture comprises organic solvent and at least 1% by weight water, at least 5% by weight water, at least 10% by weight water, no more than 20% by weight water, no more than 15% by weight water, no more than 10% by weight water, about 1% by weight to about 20% by weight water, about 5% by weight to about 15% by weight water, about 8% by weight to about 12% by weight water, or about 10% by weight water, wherein the weight % of water is relative to the weight of organic solvent in the mixture. In certain embodiments, the mixture comprises organic solvent and about 5% by weight to about 15% by weight water, relative to the amount of organic solvent. In other embodiments, the organic solvent comprises about 8% by weight to about 12% by weight water. In some embodiments, the mixture comprises organic solvent and about 10% by weight water. In certain embodiments, the mixture comprises organic solvent, wherein the organic solvent comprises one or more alcohols; and water, wherein the water is present in about 5% by weight to about 15% by weight, about 8% by weight to about 12% by weight, or about 10% by weight, wherein the weight % of water is relative to the amount of organic solvent. In still further embodiments, the mixture comprises organic solvent, wherein the organic solvent comprises ethanol, n-propanol, or isopropanol, or any combinations thereof; and water, wherein the water is present in about 5% by weight to about 15% by weight, about 8% by weight to about 12% by weight, or about 10% by weight relative to the amount of organic solvent. In still further embodiments, the mixture comprises organic solvent, wherein the organic solvent comprises isopropanol; and water, wherein the water is present in about 5% by weight to about 15% by weight, about 8% by weight to about 12% by weight, or about 10% by weight relative to the amount of organic solvent. In certain embodiments, the mixture comprises water and organic solvent at a volume ratio of less than 3:7. In certain embodiments, the mixture comprises water and organic solvent at a volume ratio of less than 1:4. In certain embodiments, the mixture comprises water and organic solvent at a volume ratio of less than 1:3, less than 1:4, less than 1:5, less than 1:6, less than 1:7, less than 1:8, or less than 1:9 by volume. In certain embodiments, the ratio is about 1:9. In any of these embodiments, the organic solvent may comprise one or more $C_1$-$C_8$, or $C_1$-$C_6$, or $C_1$-$C_4$ alcohols. In some embodiments, the organic solvent comprises ethanol and n-propanol. In certain embodiments, the organic solvent comprises isopropanol. In certain embodiments, the organic solvent is isopropanol. In some embodiments, a mixture comprising water and organic solvent at a volume ratio of less than 3:7 by volume (such as less than 1:4, for example about 1:9) results in a higher yield of a crystalline form of Compound 1 than a process using a mixture with a higher ratio of water and organic solvent.

In certain embodiments, the pH of the mixture is adjusted with hydrochloric acid by adding aqueous solution of hydrochloric acid to the mixture formed by the free base and the organic solvent, and optionally water. For example, in some embodiments, the hydrochloric acid is concentrated hydrochloride acid. In certain embodiments, the hydrochloride acid is added as an aqueous solution comprising from about 30% to about 45% by weight hydrochloric acid, or about 30% to about 40% by weight hydrochloric acid, or about 35% to about 40% by weight hydrochloric acid, or about 37% by weight hydrochloric acid. In some embodiments, aqueous hydrochloric acid of a different strength is used, for example 20% by weight, or 15% by weight, or 10% by weight, or 5% by weight aqueous hydrochloric acid. In other embodiments, the pH of the mixture is adjusted with hydrochloric acid by bubbling gaseous hydrogen chloride through the mixture to form hydrochloric acid. In some embodiments of the methods provided herein, the pH of the mixture is adjusted to between 3.5 to 4.5, or to between 3.6 to 4.4, or to between 3.7 to 4.3, or to between 3.8 to 4.2, or to between 3.9 to 4.1, or about 4.0 by the addition of hydrochloric acid.

In some embodiments, the mixture is stirred at a temperature of less than 50° C. until a precipitate is formed. In some embodiments, the mixture is stirred at a temperature of 45° C. or less, 40° C. or less, 35° C. or less, 30° C. or less, 25° C. or less, or 20° C. or less to until a precipitate is formed. In certain embodiments, the mixture is stirred at a temperature between 20° C. to 45° C., between 20° C. to 40° C., between 20° C. to 35° C., between 25° C. to 45° C., between 25° C. to 40° C., or between 25° C. to 35° C. until a precipitate is formed. In some embodiments, the mixture is stirred at a temperature of 30° C. or less until a precipitate is formed. In certain embodiments, stirring the mixture at a temperature of less than 50° C. (such as, for example, between 20° C. to 40° C., or between 25° C. to 35° C., or about 30° C.) until a precipitate is formed results in a higher yield of a crystalline form of Compound 1 from the process than stirring the mixture at a higher temperature.

In certain embodiments, after the precipitate is formed, it is isolated to produce the isolated precipitate. In certain embodiments, the precipitate is isolated directly from the mixture to form the isolated precipitate. In other embodiments, one or more steps occur after forming the precipitate prior to isolating the precipitate to form the isolated precipitate, such as one or more recrystallization steps. The precipitate may be isolated by any suitable means, such as centrifugation, filtration, or other means, to form an isolated precipitate. The isolated precipitate may undergo one or more additional steps (such as one or more wash steps) prior to being dried under reduced pressure.

In certain embodiments, which may be combined with any other embodiments described herein, water is added at one or more steps prior to drying the isolated precipitate under reduced pressure. For example, in some embodiments, the free base is combined with organic solvent and water to form a mixture; or water is added to the mixture formed by combining the free base and the organic solvent; or water is added with hydrochloric acid to adjust the pH of the mixture; or water is added to the mixture after the pH has been adjusted; or water is added to the mixture after the precipitate is formed but prior to isolating the precipitate; or water is added during or before or after any of the additional steps described herein, such as recrystallization or washing. In some embodiments, water is added two or more times during the method, such as being combined with the organic solvent and the free base to form a mixture, and while adjusting the pH of the mixture by addition of hydrochloric acid.

A. Water and Organic Solvent Content

In some embodiments, the isolated precipitate is dried under reduced pressure until a water content of between 6.5% by weight to 10% by weight is reached to produce Compound 1. In certain embodiments, the isolated precipitate is dried under reduced pressure, such as reduced pressures described here, until a water content of between 6.5% by weight, 6.6% by weight 6.7% by weight, 6.8% weight, 6.9% by weight, 7.0% by weight, 7.1% by weight, 7.2% by weight, 7.3% by weight, 7.4% by weight, 7.5% by weight, 7.6% by weight, 7.7% by weight, 7.8% by weight, 7.9% by weight, or 8.0% by weight to 8.4% by weight, 8.5% by weight, 8.6% by weight 8.7% by weight, 8.8% weight, 8.9% by weight, 9.0% by weight, 9.1% by weight, 9.2% by weight, 9.3% by weight, 9.4% by weight, 9.5% by weight, 9.6% by weight 9.7% by weight, 9.8% weight, 9.9% by weight, or 10.0% by weight is reached. In some embodiments, the isolated precipitate is dried under reduced pressure until a water content of between 7.5% by weight to 9.0% by weight is reached to produce Compound 1. In certain embodiments, the isolated precipitate is dried under reduced pressure until a water content of between 7.6% by weight to 8.8% by weight is reached to produce Compound 1. In still further embodiments, the isolated precipitate is dried under reduced pressure until a water content of about 8.2% by weight is reached to produce Compound 1. The water content of the isolated precipitate includes the water present in the trihydrate form (Compound 1).

In some embodiments, the isolated precipitate is dried under reduced pressure, such as reduced pressures described here, until the organic solvent content is less than about 6000 ppm. In some embodiments, it is dried under reduced pressure until the organic solvent content is less than about 5500 ppm, less than about 5000 ppm, less than about 4500 ppm, less than about 4000 ppm, less than about 3500 ppm, less than about 3000 ppm, less than about 2500 ppm, or less than about 2000 ppm. In certain embodiments, it is dried under reduced pressure until the organic solvent content is less than about 5000 ppm, or less than about 4000 ppm. In some embodiments, the organic solvent comprises one or more alcohols. In some embodiments, the organic solvent comprises one or more $C_1$-$C_8$, or $C_1$-$C_6$, or $C_1$-$C_4$ alcohols. In certain embodiments, the organic solvent comprises isopropanol, n-propanol, ethanol, or methanol, or any combinations thereof. In some embodiments, the organic solvent comprise ethanol and n-propanol. In some embodiments, the organic solvent comprises isopropanol.

B. Drying Conditions

In some embodiments, the reduced pressure used to dry the isolated precipitate is between about 20 mm Hg to about 60 mm Hg, or between about 20 mm Hg to about 55 mm Hg, or between about 20 mm Hg to about 50 mm Hg, or between about 25 mm Hg to about 50 mm Hg, or about 25 mm Hg to about 45 mm Hg, or about 30 mm Hg to about 40 mm Hg, or about 35 mm Hg. In some embodiments, the reduced pressure is between about 20 mm Hg to about 60 mm Hg. In other embodiments, the reduced pressure is from about 25 mm Hg to about 50 mm Hg. In certain embodiments, the reduced pressure is from about 30 mm Hg to about 50 mm Hg. In still further embodiments, the reduced pressure is from about 30 mm Hg to about 40 mm Hg, or about 35 mm Hg.

In some embodiments of the methods provided herein, the isolated precipitate is dried under reduced pressure at a temperature between about 10° C. to about 70° C., or between about 20° C. to about 60° C., or between about 25° C. to about 55° C., or between about 30° C. to about 50° C. In some embodiments, the isolated precipitate is dried under reduced pressure in one or more steps, for example, wherein the temperature of the isolated precipitate is changed over time during the drying process. In certain embodiments, drying the isolated precipitate step-wise over a range of temperatures results in a composition (such as a bulk composition) comprising Compound 1 with a lower residual organic solvent level than is achieved drying the isolated precipitate at single temperature or narrower range of temperatures. For example, in some embodiments, drying the isolated precipitate step-wise produces a composition (such as a bulk composition) comprising Compound 1 with a residual organic solvent content of less than 6000 ppm. In other embodiments, drying the isolated precipitate step-wise produces a composition (such as a bulk composition) comprising Compound 1 with a residual organic solvent content of less than about 5000 ppm, or less than about 4000 ppm, or less than about 3000 ppm, or less than about 2000 ppm. In some embodiments, the organic solvent comprises one or more alcohols. In some embodiments, the organic solvent comprises one or more $C_1$-$C_8$, or $C_1$-$C_6$, or $C_1$-$C_4$ alcohols. In certain embodiments, the organic solvent comprises iso-propanol, n-propanol, ethanol, or methanol, or any combinations thereof. In some embodiments, the organic solvent comprises ethanol and n-propanol. In still further embodiments, the organic solvent comprises isopropanol.

In some embodiments, the isolated precipitate is dried under reduced pressure at a temperature between about 10° C. to about 50° C., and then at a temperature between about 35° C. to about 70° C. to produce Compound 1. In certain embodiments, the isolated precipitate is dried under reduced pressure at a temperature between about 20° C. to about 50° C., and then at a temperature between about 35° C. to about 60° C.; or between about 25° C. to about 45° C., and then at a temperature between about 40° C. to about 55° C. In certain embodiments, the isolated precipitate is dried under reduced pressure at a temperature between about 20° C. to about 40° C.; then at a temperature between about 30° C. to about 50° C.; then at a temperature between about 35° C. to about 55° C.; and then at a temperature between about 40° C. to about 60° C. In certain embodiments, the isolated precipitate is dried under reduced pressure at a temperature between about 25° C. to about 35° C., then at a temperature between about 35° C. to about 45° C., then at a temperature between about 40° C. to about 50° C., and then at a temperature between about 45° C. to about 55° C.

In some embodiments, the isolated precipitate is dried under reduced pressure for a specified period of time, and a specified temperature or range of temperatures. For example, in certain embodiments, performing a step-wise drying comprises drying the isolated precipitate at the specified temperature or temperature range for a particular period of time. In certain embodiments, drying the isolated precipitate in such a way provides a composition comprising Compound 1 (such as a bulk composition) with a lower level of residual organic solvent than would otherwise be achieved. In some embodiments, the isolated precipitate is dried under reduced pressure at a temperature between about 10° C. to about 50° C. for about 0.5 hours to about 10 hours, and then at a temperature between about 35° C. to about 70° C. for about 0.5 hours to about 10 hours to produce Compound 1 or a bulk composition comprising Compound 1. In certain embodiments, the isolated precipitate is dried under reduced pressure at a temperature between about 20° C. to about 50° C. for about 0.5 hours to about 10 hours, and then at a temperature between about 35° C. to about 60° C. for about 0.5 hours to about 10 hours; or between about 25° C. to about 45° C. for about 0.5 hours to about 10 hours, and then at a temperature between about 40° C. to about 55° C. for about 0.5 hours to about 10 hours. In certain embodiments, the isolated precipitate is dried under reduced pressure at a temperature between about 20° C. to about 40° C. for about 0.5 hours to about 4 hours; then at a temperature between about 30° C. to about 50° C. for about 0.5 hours to about 4 hours; then at a temperature between about 35° C. to about 55° C. for about 0.5 hours to about 4 hours; and then at a temperature between about 40° C. to about 60° C. In certain embodiments, the step of drying the isolated precipitate at a temperature of about 40° C. to about 60° C. is undertaken for about 0.5 to 10 hours, or for about 2 to 10 hours, or for about 3 to 7 hours. In certain embodiments, the isolated precipitate is dried under reduced pressure at a temperature between about 25° C. to about 35° C. for about 0.5 hours to about 3 hours; then at a temperature between about 35° C. to about 45° C. for about 0.5 hours to about 3 hours; then at a temperature between about 40° C. to about 50° C. for about 0.5 hours to about 3 hours; and then at a temperature between about 45° C. to about 55° C.

In still other embodiments, the isolated precipitate is dried under reduced pressure at a temperature between about 25° C. to about 35° C. for about 0.5 to about 2.5 hours; then at a temperature between about 35° C. to about 45° C. for about 0.5 to about 2.5 hours; then at a temperature between about 40° C. to about 50° C. for about 0.5 to about 2.5 hours; and then at a temperature between about 45° C. to about 55° C. In certain embodiments, the step of drying the isolated precipitate at a temperature of about 45° C. to about 55° C. is undertaken for about 0.5 to 15 hours, or for about 2 to 12 hours, or for about 3 to 10 hours, or for about 3 to 7 hours, or for about 4 to 8 hours. In still other embodiments, the isolated precipitate is dried under reduced pressure at a temperature about 30° C. for about 0.5 to about 2.5 hours; then at a temperature about 40° C. for about 0.5 to about 2.5 hours; then at a temperature of about 45° C. for about 0.5 to about 2.5 hours; and then at a temperature of about 50° C. In certain embodiments, the step of drying the isolated precipitate at a temperature of about 50° C. is undertaken for about 0.5 to 15 hours, or for about 2 to 12 hours, or for about 3 to 10 hours, or for about 3 to 7 hours, or for about 4 to 8 hours.

In other embodiments of the methods provided herein, the isolated precipitate is dried under reduced pressure for between about 2 hours to about 20 hours, between about 2 hours to about 18 hours, between about 2 hours to about 16 hours, between about 2 hours to about 14 hours, between about 2 hours to about 12 hours, between about 2 hours to about 10 hours, between about 2 hours to about 8 hours, between about 2 hours to about 6 hours, about 3 hours to about 20 hours, between about 3 hours to about 18 hours, between about 3 hours to about 16 hours, between about 3 hours to about 14 hours, between about 3 hours to about 12 hours, between about 3 hours to about 10 hours, between about 3 hours to about 8 hours, between about 3 hours to about 6 hours, about 5 hours to about 20 hours, between about 5 hours to about 18 hours, between about 5 hours to about 16 hours, between about 5 hours to about 14 hours, between about 5 hours to about 12 hours, between about 5 hours to about 10 hours, between about 5 hours to about 8 hours, between about 7 hours to about 20 hours, between about 7 hours to about 18 hours, between about 7 hours to about 16 hours, between about 7 hours to about 14 hours, between about 7 hours to about 12 hours, or between about 7 hours to about 10 hours. In other embodiments of the methods provided herein, the isolated precipitate is dried under reduced pressure for between about 3 hours to about 10 hours. In other embodiments, the isolated precipitate is dried under reduced pressure for between about 5 hours to about 10 hours. In still further embodiments, the isolated precipitate is dried under reduced pressure for between about 7 hours to about 10 hours.

In some embodiments, between about 150 kg to about 400 kg or between about 200 kg to about 300 kg of isolated precipitate is dried under reduced pressure for between about 3 hours to about 10 hours, or between about 5 hours to about 10 hours, or between about 7 hours to about 10 hours to produce Compound 1. In certain embodiments, the isolated precipitate (such as between about 150 kg to about 400 kg) is dried under reduced pressure (for example between about 3 hours to about 12 hours, or between about 5 hours to about 12 hours, or between about 3 hours to about 10 hours, or between about 5 hours to about 10 hours, or between about 7 hours to about 10 hours) until there is less than about 6000 ppm organic solvent, or less than about 5000 ppm organic solvent, or less than about 4000 ppm organic solvent, or less than about 3000 ppm organic solvent, or less than about 2000 ppm organic solvent is reached, to produce Compound 1. In some embodiments, the organic solvent comprises one or more alcohols. In some embodiments, the organic solvent comprises one or more $C_1$-$C_8$, or $C_1$-$C_6$, or $C_1$-$C_4$ alcohols. In certain embodiments, the organic solvent comprises isopropanol, n-propanol, ethanol, or methanol, or any combinations thereof. In some embodiments, the organic solvent comprises ethanol and n-propanol. In still further embodiments, the organic solvent comprises isopropanol.

In some embodiments, between about 150 kg to about 400 kg or between about 200 kg to about 300 kg of isolated precipitate is dried under reduced pressure of from about 20 mm Hg to about 60 mm Hg, or from about 25 mm Hg to about 45 mm Hg, or about 35 mm Hg, for between about 3 hours to about 15 hours, or between about 5 hours to about 12 hours, or between about 7 hours to about 10 hours to produce Compound 1. In certain embodiments, the isolated precipitate (such as between about 150 kg to about 400 kg) is dried under reduced pressure (for example from about 20 mm Hg to about 60 mm Hg, or from about 25 mm Hg to about 45 mm Hg, or about 35 mm Hg, for example between about 3 hours to about 15 hours, or between about 5 hours to about 12 hours, or between about 7 hours to about 10 hours) until there is less than about 6000 ppm organic solvent, or less than about 5000 ppm organic solvent, or less than about 4000 ppm organic solvent, or less than about 3000 ppm organic solvent, or less than about 2000 ppm organic solvent is reached, to produce Compound 1. In some embodiments, the organic solvent comprises one or more alcohols. In some embodiments, the organic solvent comprises one or more $C_1$-$C_8$, or $C_1$-$C_6$, or $C_1$-$C_4$ alcohols. In certain embodiments, the organic solvent comprises isopropanol, n-propanol, ethanol, or methanol, or any combinations thereof. In some embodiments, the organic solvent comprises ethanol and n-propanol. In still further embodiments, the organic solvent comprises isopropanol.

For any of the methods of drying the isolated precipitate provided herein, in some embodiments the temperature recited is the temperature of the isolated precipitate during drying. In other embodiments, it is the temperature of one or more heating elements that is contacting at least part of the isolated precipitate. For example, in some embodiments the temperature of the isolated precipitate is controlled during drying using a jacketed vessel. In some embodiments, the jacketed vessel is a jacketed batch reactor. In certain embodiments, the jacketed vessel is a jacketed vacuum dryer, such as a cone dryer, spiral dryer, or paddle dryer. Thus, in some embodiments, the temperature recited in the methods of drying the isolated precipitate is the temperature of the jacket of the jacketed vessel. In some embodiments, the isolated precipitate is dried using a cone dryer with a jacket, and the temperature recited in the method is the temperature of the jacket.

In some embodiments, the use of one of the specified temperatures or pressures or times, or ranges of temperature or pressures or times, or any combinations thereof, results in a bulk composition comprising Compound 1 that has a particular stability, or organic solvent content, or water content, or ratio of trihydrate to anhydrous form, or XRPD spectra, or various combinations of these, as described herein. In some embodiments, the temperatures or pressures or times, or ranges thereof, or combinations of any of the forgoing, as described herein for drying the isolated precipitate may be combined with, for example, any of the quantities of precipitate or isolated precipitate or free base or Compound 1 used in the described process; or one or more additional steps, such as recrystallization or washing; or any of the other conditions or steps described herein.

C. Quantities

In some embodiments, the amount of time required to dry the isolated precipitate to produce Compound 1 is related to the amount of Compound 1 being made, or the amount of the free base used, or the amount of precipitate that is isolated, or the amount of isolated precipitate that is dried. In some embodiments, at least about 100 kg of the free base (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester is combined with the organic solvent, at least about 150 kg of the free base is combined with the organic solvent, at least about 175 kg of the free base is combined with the organic solvent, at least about 200 kg of the free base is combined with the organic solvent, at least about 250 kg of the free base is combined with the organic solvent, at least about 300 kg of the free base is combined with the organic solvent, at least about 350 kg of the free base is combined with the organic solvent, at least about 400 kg of the free base is combined with the organic solvent, at least about 450 kg of the free base is combined with the organic solvent, or at least about 500 kg of the free base is combined with the organic solvent. In some embodiments, for example using a large-capacity reactor, at least about 1 metric ton of the free base is combined with the organic solvent. In some embodiments, between about 100 kg to about 2,000 kg of the free base is combined with the organic solvent, between about 100 kg to about 1,000 kg of the free base is combined with the organic solvent, between about 100 kg to about 800 kg of the free base is combined with the organic solvent, between about 100 kg to about 600 kg of the free base is combined with the organic solvent, between about 100 kg to about 400 kg of the free base is combined with the organic solvent, between about 150 kg to about 2,000 kg of the free base is combined with the organic solvent, between about 150 kg to about 1,000 kg of the free base is combined with the organic solvent, between about 150 kg to about 800 kg of the free base is combined with the organic solvent, between about 150 kg to about 600 kg of the free base is combined with the organic solvent, between about 150 kg to about 400 kg of the free base is combined with the organic solvent, between about 150 kg to about 300 kg of the free base is combined with the organic solvent, between about 150 kg to about 250 kg of the free base is combined with the organic solvent, between about 200 kg to about 350 kg of the free base is combined with the organic solvent, or between about 200 kg to about 300 kg of the free base is combined with the organic solvent. As described herein, in some embodiments the free base is combined with organic solvent and water to make the mixture. Thus, for any of the amounts of free base that are combined with organic solvent as described herein, in some embodiments that amount of free base is combined with organic solvent and water to form the mixture.

In some embodiments, at least about 100 kg of precipitate is isolated, at least about 150 kg of precipitate is isolated, at least about 175 kg of precipitate is isolated, at least about 200 kg of precipitate is isolated, at least about 250 kg of precipitate is isolated, at least about 300 kg of precipitate is isolated, at least about 350 kg of precipitate is isolated, at least about 400 kg of precipitate is isolated, at least about 450 kg of precipitate is isolated, or at least about 500 kg of precipitate is isolated. In certain embodiments, for example using a large-capacity reactor, at least 1 metric ton of precipitate is isolated. In some embodiments, between about 100 kg to about 2,000 kg of precipitate is isolated, between about 100 kg to about 1,000 kg of precipitate is isolated, between about 100 kg to about 800 kg of precipitate is isolated, between about 100 kg to about 600 kg of precipitate is isolated, between about 100 kg to about 400 kg of precipitate is isolated, between about 150 kg to about 2,000 kg of precipitate is isolated, between about 150 kg to about 1,000 kg of precipitate is isolated, between about 150 kg to about 800 kg of precipitate is isolated, between about 150 kg to about 600 kg of precipitate is isolated, between about 150 kg to about 400 kg of precipitate is isolated, between about 150 kg to about 300 kg of precipitate is isolated, between about 150 kg to about 250 kg of precipitate is isolated, between about 200 kg to about 350 kg of precipitate is isolated, or between about 200 kg to about 300 kg of precipitate is isolated.

In some embodiments, at least about 100 kg of isolated precipitate is dried, at least about 150 kg of isolated precipitate is dried, at least about 175 kg of isolated precipitate is dried, at least about 200 kg of isolated precipitate is dried, at least about 250 kg of isolated precipitate is dried, at least about 300 kg of isolated precipitate is dried, at least about 350 kg of isolated precipitate is dried, at least about 400 kg of isolated precipitate is dried, at least about 450 kg of isolated precipitate is dried, or at least about 500 kg of isolated precipitate is dried. In commercial, for example using a large-capacity dryer, at least 1 metric ton of isolated precipitate is dried. In some embodiments, between about 100 kg to about 2,000 kg of isolated precipitate is dried, between about 100 kg to about 1,000 kg of isolated precipitate is dried, between about 100 kg to about 800 kg of isolated precipitate is dried, between about 100 kg to about 600 kg of isolated precipitate is dried, between about 100 kg to about 400 kg of isolated precipitate is dried, between about 150 kg to about 2,000 kg of isolated precipitate is dried, between about 150 kg to about 1,000 kg of isolated precipitate is dried, between about 150 kg to about 800 kg of isolated precipitate is dried, between about 150 kg to about 600 kg of isolated precipitate is dried, between about 150 kg to about 400 kg of isolated precipitate is dried, between about 150 kg to about 300 kg of isolated precipitate is dried, between about 150 kg to about 250 kg of isolated precipitate is dried, between about 200 kg to about 350 kg of isolated precipitate is dried, or between about 200 kg to about 300 kg of isolated precipitate is dried.

In still other embodiments, at least about 100 kg of Compound 1 is produced, at least about 150 kg of Compound 1 is produced, at least about 175 kg of Compound 1 is produced, at least about 200 kg of Compound 1 is produced, at least about 250 kg of Compound 1 is produced, at least about 300 kg of Compound 1 is produced, at least about 350 kg of Compound 1 is produced, at least about 400 kg of Compound 1 is produced, at least about 450 kg of Compound 1 is produced, or at least about 500 kg of Compound 1 is produced. In certain embodiments, for example using a commercial production facility, at least 1 metric ton of Compound 1 is produced. In some embodiments, between about 100 kg to about 2,000 kg of Compound 1 is produced, between about 100 kg to about 1,000 kg of Compound 1 is produced, between about 100 kg to about 800 kg of Compound 1 is produced, between about 100 kg to about 600 kg of Compound 1 is produced, between about 100 kg to about 400 kg of Compound 1 is produced, between about 150 kg to about 2,000 kg of Compound 1 is produced, between about 150 kg to about 1,000 kg of Compound 1 is produced, between about 150 kg to about 800 kg of Compound 1 is produced, between about 150 kg to about 600 kg of Compound 1 is produced, between about 150 kg to about 400 kg of Compound 1 is produced, between about 150 kg to about 300 kg of Compound 1 is produced, between about 150 kg to about 250 kg of Compound 1 is produced, between about 200 kg to about 350 kg of Compound 1 is produced, or between about 200 kg to about 300 kg of Compound 1 is produced.

D. Additional Steps

The methods of producing a bulk composition comprising Compound 1 provided herein may, in some embodiments, comprise one or more additional steps.

For example, in some embodiments, after or during stirring the mixture until a precipitate is formed in step (c), additional solvent is added to the mixture before the precipitate is isolated. In some embodiments, the additional solvent comprises organic solvent. In certain embodiments, the organic solvent comprises one or more alcohols. In some embodiments, the organic solvent comprises one or more $C_1$-$C_8$, or $C_1$-$C_6$, or $C_1$-$C_4$ alcohols. In certain embodiments, the organic solvent comprises isopropanol, n-propanol, ethanol, or methanol, or any combinations thereof. In some embodiments, the organic solvent comprises ethanol and n-propanol. In still further embodiments, the organic solvent comprises isopropanol. In some embodiments, the mixture in step (c) is adjusted such that it comprises water and organic solvent, wherein the water is present at between 5% to 15% by weight, or about 8% to about 12% by weight. In some embodiments, the mixture in step (c) is adjusted such that it comprises water and organic solvent at a volume ratio of less than 3:7. In some embodiments, the mixture in step (c) is adjusted such that it comprises water and organic solvent at a volume ratio of less than 1:4. In certain embodiments, the mixture in step (c) is adjusted such that it comprises water and organic solvent at a volume ratio of less than 1:3, less than 1:4, less than 1:5, less than 1:6, less than 1:7, less than 1:8, or less than 1:9 by volume. In certain embodiments, the ratio is about 1:9. In some embodiments, the organic solvent comprises one or more alcohols. In any of these embodiments, the organic solvent may comprise one or more $C_1$-$C_8$, or $C_1$-$C_6$, or $C_1$-$C_4$ alcohols. In some embodiments, the organic solvent comprises ethanol and n-propanol. In certain embodiments, the organic solvent comprises isopropanol. In certain embodiments, the organic solvent is isopropanol.

a. Recrystallization

In some embodiments, which may be combined with any of the other embodiments described herein, the method of producing Compound 1 comprises one or more recrystallization steps. Thus, for example, in some embodiments, after the isolated precipitate is formed in step (d), and before the isolated precipitate is dried in step (e), at least a portion of the isolated precipitate is dissolved in a recrystallization solvent to form a recrystallization mixture, the recrystallization mixture is stirred until a recrystallized precipitate is formed, and the recrystallized precipitate is isolated to form an isolated precipitate. This isolated precipitate may, for example, be taken on to step (e) and dried to form Compound 1, or may, in some embodiments, be subject to one or more additional steps, such as another recrystallization, or a washing step, or a combination thereof.

Any suitable recrystallization conditions may be used. In certain embodiments, a recrystallization solvent comprising water and organic solvent is used. In some embodiments, the organic solvent comprises one or more alcohols, for example isopropanol, n-propanol, ethanol, or methanol, or any combinations thereof. In some embodiments, the recrystallization solvent comprises water and organic solvent, wherein the water is present at between 5% to 15% by weight, or about 8% to about 12% by weight. In some embodiments, the recrystallization solvent comprises water and organic solvent at a volume ratio of less than 3:7. In certain embodiments, the recrystallization solvent comprises water and organic solvent at a volume ratio of less than 1:4. In certain embodiments, recrystallization solvent comprises water and organic solvent at a volume ratio of less than 1:3, less than 1:4, less than 1:5, less than 1:6, less than 1:7, less than 1:8, or less than 1:9 by volume. In certain embodiments, the ratio is about 1:9. In any of these embodiments, the organic solvent may comprise one or more $C_1$-$C_8$, or $C_1$-$C_6$, or $C_1$-$C_4$ alcohols. In some embodiments, the organic solvent comprises ethanol and n-propanol. In certain embodiments, the organic solvent comprises isopropanol. In certain embodiments, the organic solvent is isopropanol. In some embodiments, using a recrystallization solvent comprising water and organic solvent at a volume ratio of less than 3:7 by volume (such as less than 1:4, for example about 1:9) produces a crystalline form of Compound 1 with a higher yield than using a higher ratio of water to organic solvent (such as isopropanol). In certain embodiments, the recrystallization mixture is filtered prior to stirring until a recrystallized precipitate is formed. In some embodiments, the recrystallized precipitate is isolated by centrifugation, filtration, or other means to form an isolated precipitate.

In some embodiments, when recrystallizing at least a portion of the isolated precipitate, the recrystallization mixture is stirred at a temperature of less than 50° C. In some embodiments, the recrystallization mixture is stirred at a temperature of 45° C. or less, 40° C. or less, 35° C. or less, 30° C. or less, 25° C. or less, or 20° C. or less. In certain embodiments, the recrystallization mixture is stirred at a temperature between 20° C. to 45° C., between 20° C. to 40° C., between 20° C. to 35° C., between 25° C. to 45° C., between 25° C. to 40° C., or between 25° C. to 35° C. In some embodiments, the recrystallization mixture is stirred at a temperature of 30° C. or less. In certain embodiments, recrystallizing at least a portion of the isolated precipitate at a temperature of less than 50° C. (such as, for example, between 20° C. to 40° C., or between 25° C. to 35° C., or about 30° C.) produces a crystalline form of Compound 1 with a higher yield than using a higher recrystallization temperature.

In certain embodiments, recrystallizing at least a portion of the isolated precipitate at a temperature of less than 50° C. (such as, for example, between 20° C. to 40° C., or between 25° C. to 35° C., or about 30° C.), and using a recrystallization solvent comprising water and organic solvent at a volume ratio of less than 3:7 by volume (such as less than 1:4, for example about 1:9) produces a crystalline form of Compound 1 with a higher yield than using a higher recrystallization temperature or a higher ratio of water to organic solvent. In some embodiments, using isopropanol as the organic solvent in recrystallization also contributes to a higher yield, compared to using a different organic solvent in the same process.

Thus, in some embodiments, the method of making Compound 1 (such as methods of making a bulk composition comprising Compound 1) comprises combining the free base (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester with organic solvent to form a mixture; adjusting the pH of the mixture to between 3.5 and 4.5 by the addition of hydrochloric acid; stirring the mixture until a precipitate is formed; isolating the precipitate; dissolving at least a portion of the isolated precipitate in a recrystallization solvent to form a recrystallization mixture; stirring the recrystallization mixture until a recrystallized precipitate is formed; isolating the recrystallized precipitate to form an isolated precipitate; and drying the isolated precipitate under reduced pressure to produce the trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt (Compound 1).

b. Wash Step

In other embodiments, at least a portion of the isolated precipitate is washed one or more times prior to being dried under reduced pressure. In some embodiments, at least a portion of the isolated precipitate is washed one or more times with an aqueous wash prior to being dried under reduced pressure. In some embodiments, the isolated precipitate being washed one or more times was isolated from a recrystallization mixture. In other embodiments, the isolated precipitate being washed one or more times has not been recrystallized. In certain embodiments, the aqueous wash comprises organic solvent. In some embodiments, the organic solvent comprises one or more alcohols. In some embodiments, the organic solvent comprises one or more $C_1$-$C_8$, or $C_1$-$C_6$, or $C_1$-$C_4$ alcohols. In certain embodiments, the organic solvent comprises isopropanol, n-propanol, ethanol, or methanol, or any combinations thereof. In some embodiments, the organic solvent comprises ethanol and n-propanol. In still further embodiments, the organic solvent comprises isopropanol. In some embodiments, at least a portion of the isolated precipitate is washed one or more times with an aqueous wash prior to being dried under reduced pressure, wherein the aqueous wash comprises organic solvent and water. In some embodiments, the aqueous wash comprises water and one or more alcohols, for example water and isopropanol, n-propanol, ethanol, or methanol, or any combinations thereof. In some embodiments, the aqueous wash comprises water at about 5% to about 15% by weight, or about 8% to about 12% by weight.

In some embodiments, the aqueous wash comprises water and organic solvent at a volume ratio of less than 3:7, or less than 1:4, such as about 1:9. In some embodiments, the isolated precipitate is washed one or more times with an aqueous wash solution comprising isopropanol and water prior to being dried under reduced pressure to produce Compound 1. Thus, in some embodiments, the method of making Compound 1 (such as methods of making a bulk composition comprising Compound 1) comprises combining the free base (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester with organic solvent to form a mixture; adjusting the pH of the mixture to between 3.5 and 4.5 by the addition of hydrochloric acid; stirring the mixture until a precipitate is formed; isolating the precipitate; washing the isolated precipitate; and, after washing, drying the isolated precipitate under reduced pressure to produce the trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt (Compound 1). In some embodiments, the isolated precipitate is washed with an aqueous wash, wherein the aqueous wash comprises organic solvent and about 5% to 15% by weight water.

In some embodiments, the temperatures or solvents (including ratios or percentages of organic solvent and water), or ranges thereof, or combinations of any of the forgoing, as described herein for washing the isolated precipitate, or for recrystallization, or a combination thereof, may be combined with, for example, any of the quantities of precipitate or isolated precipitate or free base or Compound 1 used in the described process; or any of the temperatures or pressures or times, or ranges thereof, or combinations of any of these, in the drying step described herein; or any of the other conditions or steps described herein. In some embodiments, including one or more recrystallization or washing steps as described herein, or combinations thereof, in the process of making a bulk composition as described herein, results in a bulk composition comprising Compound 1 that has a particular stability, or organic solvent content, or water content, or ratio of trihydrate to anhydrous form, or XRPD spectra, or various combinations of these, as described herein.

The provided description sets forth numerous exemplary configurations, methods, parameters, and the like. It should be recognized, however, that such description is not intended as a limitation on the scope of the present disclosure, but is instead provided as a description of exemplary embodiments.

ENUMERATED EMBODIMENTS

Embodiment I-1. A bulk composition comprising a trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt, which has the following formula:

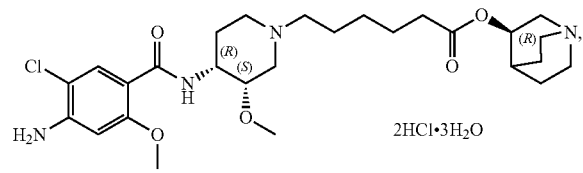

2HCl•3H$_2$O and at least one container.

Embodiment I-2. The bulk composition of embodiment I-1, comprising at least 75% by weight of the trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt, wherein the weight excludes the weight of the at least one container.

Embodiment I-3. The bulk composition of embodiment I-1 or I-2, further comprising an anhydrous form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt, wherein the ratio of the trihydrate form to the anhydrous form is at least about 4 to 1.

Embodiment I-4. The bulk composition of embodiment I-1 or I-2, comprising at least about 6.5% by weight water relative to the total weight of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt present in anhydrous or trihydrate form.

Embodiment I-5. The bulk composition of embodiment I-3, wherein the ratio of the trihydrate form to the anhydrous form is at least about 11 to 1.

Embodiment I-6. The bulk composition of any one of embodiments I-1 to I-4, comprising at least about 7.5% by weight water relative to the total weight of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt present in anhydrous or trihydrate form.

Embodiment I-7. The bulk composition of any one of embodiments I-1 to I-6, wherein the trihydrate form is in a crystalline form, and wherein the crystalline form has XRPD peaks at 7.74±0.5° and 20.95±0.5°.

Embodiment I-8. A pharmaceutical composition comprising a trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt, which has the following formula:

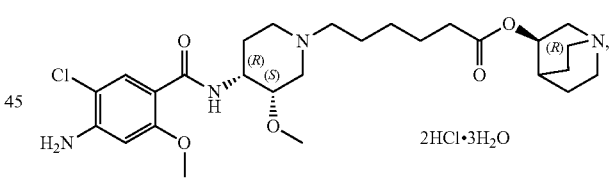

2HCl•3H$_2$O and a pharmaceutically acceptable excipient.

Embodiment I-9. The pharmaceutical composition of embodiment I-8, further comprising an anhydrous form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt, wherein the ratio of the trihydrate form to the anhydrous form is at least about 4 to 1.

Embodiment I-10. The pharmaceutical composition of embodiment I-8, comprising between about 6.5% to about 10% by weight water relative to the total weight of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt present in anhydrous or trihydrate form.

Embodiment I-11. The pharmaceutical composition of embodiment I-9, wherein the ratio of the trihydrate form to the anhydrous form is at least about 11 to 1.

Embodiment I-13. The pharmaceutical composition of any one of embodiments I-8 to I-11, comprising between about 7.5% to about 9% by weight water relative to the total weight of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt present in anhydrous or trihydrate form.

Embodiment I-14. The pharmaceutical composition of any one of embodiments I-8 to I-13, comprising less than 1% by weight of the anhydrous form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt.

Embodiment I-15. The pharmaceutical composition of any one of embodiments I-8 to I-14, wherein the trihydrate form is in a crystalline form, and wherein the crystalline form has XRPD peaks at 7.74±0.5° and 20.95±0.5°.

Embodiment I-16. A dosage form comprising the pharmaceutical composition of any one of embodiments I-8 to I-15.

Embodiment I-17. The dosage form of embodiment I-16, wherein the dosage form comprises one or more tablets or one or more capsules.

Embodiment I-18. A kit comprising the dosage form of embodiment I-16 or I-17 and packaging.

Embodiment I-19. The kit of embodiment I-18, wherein the packaging is a blister pack.

Embodiment I-20. A method of improving gastrointestinal motility in a subject in need thereof, comprising administering to the subject in need thereof a therapeutically effective amount of the pharmaceutical composition of any one of embodiments I-8 to I-15, or the dosage form of embodiments I-16 or I-17.

Embodiment I-21. The method of embodiment I-20, wherein the subject in need thereof has a gastrointestinal disorder.

Embodiment I-22. A method of treating a gastrointestinal disorder in a subject in need thereof, comprising administering to the subject in need thereof a therapeutically effective amount of the pharmaceutical composition of any one of embodiments I-8 to I-15, or the dosage form of embodiment I-16 or I-17.

Embodiment I-23. The method of embodiment I-21 or I-22, wherein the gastrointestinal disorder is selected from the group consisting of gastroesophageal reflux disease (GERD), functional dyspepsia or functional motility disorder, gastroparesis, paralytic ileus, post-operative ileus, emesis, nausea, heartburn, intestinal pseudo-obstruction, irritable bowel syndrome (IBS), constipation, enteral feeding intolerance (EFI), and esophagitis.

Embodiment I-24. The use of embodiment I-23, wherein the GERD is proton pump inhibitor (PPI) resistant GERD.

Embodiment I-25. The use of embodiment I-23, wherein the constipation is opiate induced constipation (OIC), chronic idiopathic constipation (CIC), or constipation associated with irritable bowel syndrome constipation type (IBSc).

Embodiment I-26. The use of embodiment I-23, wherein the esophagitis is erosive esophagitis (EE) or eosinophilic esophagitis (EoE).

Embodiment I-27. The use of embodiment I-23, wherein the IBS is irritable bowel syndrome constipation type (IBSc).

Embodiment I-28. The use of embodiment I-23, wherein the gastroparesis is diabetic gastroparesis, or idiopathic or functional gastroparesis.

Embodiment I-29. The use of embodiment I-21 or I-22, wherein the gastrointestinal disorder is selected from the group consisting of proton pump inhibitor (PPI) resistant GERD, emesis, gastroparesis, opiate induced constipation (OIC), chronic idiopathic constipation (CIC), erosive esophagitis (EE), eosinophilic esophagitis (EoE), functional dyspepsia (FD) or functional motility disorder (FMD), intestinal pseudo-obstruction, irritable bowel syndrome constipation type (IBSc), enteral feeding intolerance (EFI), and post-operative ileus.

Embodiment I-30. The use of embodiment I-21 or I-22, wherein the gastrointestinal disorder is selected from the group consisting of post-operative ileus, chronic grass sickness, constipation, megacolon, gastritis, gastrointestinal stasis, and abomasal emptying defect.

Embodiment I-31. The use of embodiment I-30, wherein the gastritis is atrophic gastritis.

Embodiment I-32. Use of a trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt in the manufacture of a medicament for improving gastrointestinal motility in a subject in need thereof.

Embodiment I-33. The use of embodiment I-32, wherein the subject in need thereof has a gastrointestinal disorder.

Embodiment I-34. Use of a trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt in the manufacture of a medicament for treating a gastrointestinal disorder in a subject in need thereof.

Embodiment I-35. The use of embodiment I-33 or I-34, wherein the gastrointestinal disorder is selected from the group consisting of gastroesophageal reflux disease (GERD), functional dyspepsia or functional motility disorder, gastroparesis, paralytic ileus, post-operative ileus, emesis, nausea, heartburn, intestinal pseudo-obstruction, irritable bowel syndrome (IBS), constipation, enteral feeding intolerance (EFI), and esophagitis.

Embodiment I-36. The use of embodiment I-35, wherein the GERD is proton pump inhibitor (PPI) resistant GERD.

Embodiment I-37. The use of embodiment I-35, wherein the constipation is opiate induced constipation (OIC), chronic idiopathic constipation (CIC), or constipation associated with irritable bowel syndrome constipation type (IBSc).

Embodiment I-38. The use of embodiment I-35, wherein the esophagitis is erosive esophagitis (EE) or eosinophilic esophagitis (EoE).

Embodiment I-39. The use of embodiment I-35, wherein the IBS is irritable bowel syndrome constipation type (IBSc).

Embodiment I-40. The use of embodiment I-35, wherein the gastroparesis is diabetic gastroparesis, or idiopathic or functional gastroparesis.

Embodiment I-41. The use of embodiment I-33 or I-34, wherein the gastrointestinal disorder is selected from the group consisting of proton pump inhibitor (PPI) resistant GERD, emesis, gastroparesis, opiate induced constipation (OIC), chronic idiopathic constipation (CIC), erosive esophagitis (EE), eosinophilic esophagitis (EoE), functional dyspepsia (FD) or functional motility disorder (FMD), intestinal pseudo-obstruction, irritable bowel syndrome constipation type (IBSc), enteral feeding intolerance (EFI), and post-operative ileus.

Embodiment I-42. The use of embodiment I-33 or I-34, wherein the gastrointestinal disorder is selected from the group consisting of post-operative ileus, chronic grass sickness, constipation, megacolon, gastritis, gastrointestinal stasis, and abomasal emptying defect.

Embodiment I-43. The use of embodiment 1-42, wherein the gastritis is atrophic gastritis.

Embodiment I-44. A compound for use in improving gastrointestinal motility in a subject in need thereof, wherein the compound is a trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt.

Embodiment I-45. The compound for use of embodiment I-44, wherein the subject in need thereof has a gastrointestinal disorder.

Embodiment I-46. A compound for use in treating a gastrointestinal disorder in a subject in need thereof, wherein the compound is a trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt.

Embodiment I-47. The compound for use of embodiment I-45 or I-46, wherein the gastrointestinal disorder is selected from the group consisting of gastroesophageal reflux disease (GERD), functional dyspepsia or functional motility disorder, gastroparesis, paralytic ileus, post-operative ileus, emesis, nausea, heartburn, intestinal pseudo-obstruction, irritable bowel syndrome (IBS), constipation, enteral feeding intolerance (EFI), and esophagitis.

Embodiment I-48. The compound for use of embodiment I-47, wherein the GERD is proton pump inhibitor (PPI) resistant GERD.

Embodiment I-49. The compound for use of embodiment I-47, wherein the constipation is opiate induced constipation (OIC), chronic idiopathic constipation (CIC), or constipation associated with irritable bowel syndrome constipation type (IBSc).

Embodiment I-50. The compound for use of embodiment I-47, wherein the esophagitis is erosive esophagitis (EE) or eosinophilic esophagitis (EoE).

Embodiment I-51. The compound for use of embodiment I-47, wherein the IBS is irritable bowel syndrome constipation type (IBSc).

Embodiment I-52. The compound for use of embodiment I-47, wherein the gastroparesis is diabetic gastroparesis, or idiopathic or functional gastroparesis.

Embodiment I-53. The compound for use of embodiment I-45 or I-46, wherein the gastrointestinal disorder is selected from the group consisting of proton pump inhibitor (PPI) resistant GERD, emesis, gastroparesis, opiate induced constipation (OIC), chronic idiopathic constipation (CIC), erosive esophagitis (EE), eosinophilic esophagitis (EoE), functional dyspepsia (FD) or functional motility disorder (FMD), intestinal pseudo-obstruction, irritable bowel syndrome constipation type (IBSc), enteral feeding intolerance (EFI), and post-operative ileus.

Embodiment I-54. The compound for use of embodiment I-45 or I-46, wherein the gastrointestinal disorder is selected from the group consisting of post-operative ileus, chronic grass sickness, constipation, megacolon, gastritis, gastrointestinal stasis, and abomasal emptying defect.

Embodiment I-55. The compound for use of embodiment 1-54, wherein the gastritis is atrophic gastritis.

Embodiment I-56. A pharmaceutical composition for use in improving gastrointestinal motility in a subject in need thereof, wherein the pharmaceutical composition comprises a trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt.

Embodiment I-57. The pharmaceutical composition for use of embodiment I-56, wherein the subject in need thereof has a gastrointestinal disorder.

Embodiment I-58. A pharmaceutical composition for use in treating a gastrointestinal disorder in a subject in need thereof, wherein the pharmaceutical composition comprises a trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt.

Embodiment I-59. The pharmaceutical composition for use of embodiment I-57 or I-58, wherein the gastrointestinal disorder is selected from the group consisting of gastroesophageal reflux disease (GERD), functional dyspepsia or functional motility disorder, gastroparesis, paralytic ileus, post-operative ileus, emesis, nausea, heartburn, intestinal pseudo-obstruction, irritable bowel syndrome (IBS), constipation, enteral feeding intolerance (EFI), and esophagitis.

Embodiment I-60. The pharmaceutical composition for use of embodiment I-59, wherein the GERD is proton pump inhibitor (PPI) resistant GERD.

Embodiment I-61. The pharmaceutical composition for use of embodiment I-59, wherein the constipation is opiate induced constipation (OIC), chronic idiopathic constipation (CIC), or constipation associated with irritable bowel syndrome constipation type (IBSc).

Embodiment I-62. The pharmaceutical composition for use of embodiment I-59, wherein the esophagitis is erosive esophagitis (EE) or eosinophilic esophagitis (EoE).

Embodiment I-63. The pharmaceutical composition for use of embodiment I-59, wherein the IBS is irritable bowel syndrome constipation type (IBSc).

Embodiment I-64. The pharmaceutical composition for use of embodiment 1-59, wherein the gastroparesis is diabetic gastroparesis, or idiopathic or functional gastroparesis.

Embodiment I-65. The pharmaceutical composition for use of embodiment I-57 or I-58, wherein the gastrointestinal disorder is selected from the group consisting of proton pump inhibitor (PPI) resistant GERD, emesis, gastroparesis, opiate induced constipation (OIC), chronic idiopathic constipation (CIC), erosive esophagitis (EE), eosinophilic esophagitis (EoE), functional dyspepsia (FD) or functional motility disorder (FMD), intestinal pseudo-obstruction, irritable bowel syndrome constipation type (IBSc), enteral feeding intolerance (EFI), and post-operative ileus.

Embodiment I-66. The pharmaceutical composition for use of embodiment I-57 or I-58, wherein the gastrointestinal disorder is selected from the group consisting of post-operative ileus, chronic grass sickness, constipation, megacolon, gastritis, gastrointestinal stasis, and abomasal emptying defect.

Embodiment I-67. The pharmaceutical composition for use of embodiment I-66, wherein the gastritis is atrophic gastritis.

Embodiment I-68. The method of any one of embodiments I-20 to I-27, the use of any one of embodiments I-32 to I-41, the compound for use of any one of embodiments I-44 to I-53, or the pharmaceutical composition for use of any one of embodiments I-56 to I-65, wherein the subject in need thereof is a human.

Embodiment I-69. The method of any one of embodiments I-20 to I-22 or I-27 to I-29, the use of any one of embodiments I-32 to I-34 or I-41 to I-43, the compound for use of any one of embodiments I-44 to I-46 or I-53 to I-55, or the pharmaceutical composition for use of any one of embodiments I-56 to I-58 or I-65 to I-67, wherein the subject in need thereof is a non-human animal.

Embodiment I-70. The method, use, compound for use, or pharmaceutical composition for use of embodiment I-69, wherein the non-human animal is a ruminant, an equine, a cat, a dog, a rabbit, or a guinea pig.

Embodiment I-71. The method, use, compound for use, or pharmaceutical composition for use of embodiment I-70, wherein the ruminant is a sheep, cow, yak, bison, or buffalo.

Embodiment I-72. The method, use, compound for use, or pharmaceutical composition for use of embodiment I-70, wherein the equine is a horse or a donkey.

Embodiment I-73. The method of any one of embodiments I-20 to I-29 or I-68 to I-72, the use of any one of embodiments I-32 to I-43 or I-68 to I-72, the compound for use of any one of embodiments I-44 to I-55 or I-68 to I-72, or the pharmaceutical composition for use of any one of embodiments I-56 to I-72, wherein the subject in need thereof is a newborn.

Embodiment I-74. The method of any one of embodiments I-20 to I-29 or I-68 to I-73; the use of any one of embodiments I-32 to I-43 or I-68 to I-73; the compound for use of any one of embodiments I-44 to I-55 or I-68 to I-73; or the pharmaceutical composition for use of any one of embodiments I-56 to I-67 or I-68 to I-73, wherein the pharmaceutical composition is administered parenterally.

Embodiment I-75. The method of any one of embodiments I-20 to I-29 or I-68 to I-73; the use of any one of embodiments I-32 to I-43 or I-68 to I-73; the compound for use of any one of embodiments I-44 to I-55 or I-68 to I-73; or the pharmaceutical composition for use of any one of embodiments I-56 to I-67 or I-68 to I-73, wherein the pharmaceutical composition is administered orally.

Embodiment I-76. The method of any one of embodiments I-20 to I-29 or I-68 to I-73; the use of any one of embodiments I-32 to I-43 or I-68 to I-73; the compound for use of any one of embodiments I-44 to I-55 or I-68 to I-73; or the pharmaceutical composition for use of any one of embodiments I-56 to I-67 or I-68 to I-73, wherein the pharmaceutical composition is administered through a gastric tube.

Embodiment I-77. The method of any one of embodiments I-20 to I-31 or I-68 to I-76; the use of any one of embodiments I-32 to I-43 or I-68 to I-76; the compound for use of any one of embodiments I-44 to I-55 or I-68 to I-76; or the pharmaceutical composition for use of any one of embodiments I-56 to I-67 or I-68 to I-76, wherein the trihydrate form is in a crystalline form, and wherein the crystalline form has XRPD 2-theta (2θ) peaks at 7.74±0.5° and 20.95±0.5°.

Embodiment I-78. The bulk composition of any one of embodiments I-1 to I-7; or the pharmaceutical composition of any one of embodiments I-8 to I-15; or the dosage form of embodiment I-16 or I-17; or the kit of embodiment I-18 or I-19; or the method of any one of embodiments I-20 to I-31 or I-68 to I-77; or the use of any one of embodiments I-32 to I-43 or I-68 to I-77; or the compound for use of any one of embodiments I-44 to I-55 or I-68 to I-77; or the pharmaceutical composition for use of any one of embodiments I-56 to I-67 or I-68 to I-77, wherein the trihydrate form is in a crystalline form, and wherein the crystalline form has a greater than 50% relative intensity XRPD 2-theta (2θ) peak at 7.74±0.5°, and a 100% relative intensity XRPD 2-theta (2θ) peak at 20.95°±0.5°.

Embodiment I-79. The bulk composition of any one of embodiments I-1 to I-7 or I-78; or the pharmaceutical composition of any one of embodiments I-8 to I-15 or I-78; or the dosage form of embodiment I-16 or I-17 or I-78; or the kit of embodiment I-18 or I-19 or I-78; or the method of any one of embodiments I-20 to I-31 or I-68 to I-78; or the use of any one of embodiments I-32 to I-43 or I-68 to I-78; or the compound for use of any one of embodiments I-44 to I-55 or I-68 to I-78; or the pharmaceutical composition for use of any one of embodiments I-56 to I-67 or I-68 to I-78, wherein the trihydrate form is in a crystalline form, and wherein the crystalline form has two or more XRPD 2-theta (2θ) peaks selected from the group consisting of 10.3°±0.2°, 13.6°±0.2°, 14.8°±0.2°, 15.0°±0.2°, 15.4°±0.2°, 17.5°±0.2°, 18.3°±0.2°, 18.6°±0.2°, 19.2°±0.2°, 21.3°±0.2°, 22.0°±0.2°, 23.6°±0.2°, 24.3°±0.2°, 25.2°±0.2°, 26.0°±0.2°, 27.2°±0.2°, 30.1°±0.2°, 32.4°±0.2°, 33.4°±0.2°, 38.2°±0.20, and 39.4°±0.20.

Embodiment I-80. The bulk composition of any one of embodiments I-1 to I-7, I-78, or I-79; or the pharmaceutical composition of any one of embodiments I-8 to I-15, I-78, or I-79; or the dosage form of embodiment I-16 or I-17, I-78, or I-79; or the kit of embodiment I-18 or I-19, I-78, or I-79; or the method of any one of embodiments I-20 to I-31 or I-68 to I-79; or the use of any one of embodiments I-32 to I-43 or I-68 to I-79; or the compound for use of any one of embodiments I-44 to I-55 or I-68 to I-79; or the pharmaceutical composition for use of any one of embodiments I-56 to I-67 or I-68 to I-79, wherein the trihydrate form is in a crystalline form, and wherein the crystalline form has XRPD 2-theta (2θ) peaks at 7.6°±0.2° and 20.7°±0.2°.

Embodiment I-81. The bulk composition, pharmaceutical composition, dosage form, kit, method, use, compound for use, or pharmaceutical composition for use of embodiment I-80, wherein the 7.6°±0.2° XRPD 2-theta (2θ) peak has greater than 50% relative intensity, and the 20.7°±0.2° XRPD 2-theta (2θ) peak has 100% relative intensity.

Embodiment I-82. The bulk composition, pharmaceutical composition, dosage form, kit, method, use, compound for use, or pharmaceutical composition for use of embodiment I-80 or I-81, wherein the crystalline form further has two or more XRPD 2-theta (2θ) peaks selected from the group consisting of 10.3°±0.2°, 13.6°±0.2°, 14.8°±0.2°, 15.0°±0.2°, 15.4°±0.2°, 17.5°±0.2°, 18.3°±0.2°, 18.6°±0.2°, 19.2°±0.2°, 21.3°±0.2°, 22.0°±0.2° 23.6°±0.2°, 24.3°±0.2°, 25.2°±0.2°, 26.0°±0.2°, 27.2°±0.2°, 30.1°±0.2°, 32.4°±0.2°, 33.4°±0.2°, 38.2°±0.20, and 39.4°±0.2°.

Embodiment I-83. The bulk composition of any one of embodiments I-1 to I-7, or I-78 to I-82; or the pharmaceutical composition of any one of embodiments I-8 to I-15, or I-78 to I-82; or the dosage form of embodiment I-16 or I-17, or I-78 to I-82; or the kit of embodiment I-18 or I-19, or I-78 to I-82; method of any one of embodiments I-20 to I-31 or I-68 to I-82; or the use of any one of embodiments I-32 to I-43 or I-68 to I-82; or the compound for use of any one of embodiments I-44 to I-55 or I-68 to I-82; or the pharmaceutical composition for use of any one of embodiments I-56 to I-67 or I-68 to I-82, wherein the bulk composition, pharmaceutical composition, dosage form, kit, or medicament comprises less than about 6000 ppm organic solvent.

Embodiment I-83. The bulk composition, or the pharmaceutical composition, or the dosage form, or the kit, or the method, or the compound for use, or the pharmaceutical composition for use of embodiment I-83, wherein the bulk composition, pharmaceutical composition, dosage form, kit, or medicament comprises less than about 5000 ppm, less than about 4000 ppm, less than about 3000 ppm, or less than about 2000 ppm organic solvent.

Embodiment I-84. The bulk composition, or the pharmaceutical composition, or the dosage form, or the kit, or the method, or the compound for use, or the pharmaceutical composition for use of embodiment I-82 or I-83, wherein the organic solvent comprises one or more $C_1$-$C_8$ alcohols.

Embodiment I-85. The bulk composition, or the pharmaceutical composition, or the dosage form, or the kit, or the method, or the compound for use, or the pharmaceutical composition for use of any one of embodiments I-82 to I-84, wherein the organic solvent comprises ethanol, n-propanol, or isopropanol, or a combination thereof.

Embodiment I-86. The bulk composition, or the pharmaceutical composition, or the dosage form, or the kit, or the method, or the compound for use, or the pharmaceutical composition for use of any one of embodiments I-82 to I-85, wherein the organic solvent comprises isopropanol.

Embodiment II-1. A method of making a trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt, which has the following formula:

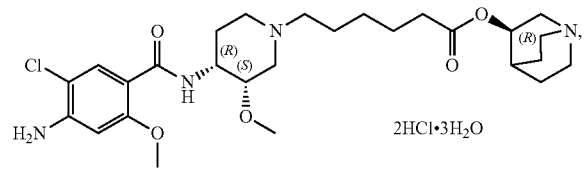

2HCl•3H$_2$O the method comprising:
(a) combining free base (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester with organic solvent to form a mixture;
(b) adjusting the pH of the mixture to between 3.5 and 4.5 by the addition of hydrochloric acid;
(c) stirring the mixture until a precipitate is formed;
(d) isolating the precipitate to form an isolated precipitate; and
(e) drying the isolated precipitate under reduced pressure until a water content of between 6.5% by weight to 10% by weight is reached to produce the trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt.

Embodiment II-2. The method of Embodiment II-1, wherein the isolated precipitate is dried under reduced pressure until the organic solvent content is less than about 6000 ppm.

Embodiment II-3. The method of Embodiment II-1 or II-2, wherein the organic solvent comprises one or more alcohols.

Embodiment II-4. The method of any one of Embodiments II-1 to II-3, wherein the organic solvent comprises ethanol, n-propanol, or isopropanol, or a combination thereof.

Embodiment II-5. The method of any one of Embodiments II-1 to II-4, wherein the organic solvent comprises isopropanol.

Embodiment II-6. The method of any one of Embodiments II-1 to II-5, wherein the free base is combined with water and organic solvent to form the mixture.

Embodiment II-7. The method of any one of Embodiments II-1 to II-6, wherein the free base is combined with water and organic solvent to form the mixture, wherein the water is present in the mixture at about 5% to about 15% by weight relative to the organic solvent.

Embodiment II-8. The method of any one of Embodiments II-1 to II-7, wherein the organic solvent combined with the free base comprises one or more alcohols.

Embodiment II-9. The method of any one of Embodiments II-1 to II-8, wherein the organic solvent combined with the free base comprises one or more $C_1$-$C_8$ alcohols.

Embodiment II-10. The method of any one of Embodiments II-1 to II-9, wherein the organic solvent combined with the free base comprises isopropanol.

Embodiment II-11. The method of any one of Embodiments II-1 to II-10, wherein the isolated precipitate is dried under reduced pressure at a temperature between about 20° C. to about 60° C.

Embodiment II-12. The method of any one of Embodiments II-1 to II-11, wherein the isolated precipitate is dried under reduced pressure for between about 3 hours to about 12 hours.

Embodiment II-13. The method of any one of Embodiments II-1 to II-12, wherein the isolated precipitate is dried under reduced pressure at a temperature between about 25° C. to about 35° C., then at a temperature between about 30° C. to about 45° C., then at a temperature between about 30° C. to about 50° C., and then at a temperature between about 30° C. to about 55° C.

Embodiment II-14. The method of any one of Embodiments II-1 to II-13, wherein the isolated precipitate is dried under reduced pressure at a temperature between about 25° C. to about 35° C., then at a temperature between about 35° C. to about 45° C., then at a temperature between about 40° C. to about 50° C., and then at a temperature between about 45° C. to about 55° C.

Embodiment II-15. The method of any one of Embodiments II-1 to II-14, wherein the isolated precipitate is dried under reduced pressure at a temperature between about 25° C. to about 35° C. for about 0.5 to about 2.5 hours; then at a temperature between about 35° C. to about 45° C. for about 0.5 to about 2.5 hours; then at a temperature between about 40° C. to about 50° C. for about 0.5 to about 2.5 hours; and then at a temperature between about 45° C. to about 55° C.

Embodiment II-16. The method of any one of Embodiments II-1 to II-15, wherein the isolated precipitate is dried under reduced pressure until a water content of between 7.5% by weight to 9.0% by weight is reached to produce the trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt.

Embodiment II-17. The method of any one of Embodiments II-1 to II-16, wherein the reduced pressure is from about 20 mm Hg to about 60 mm Hg.

Embodiment II-18. The method of any one of Embodiments II-1 to II-17, wherein the reduced pressure is from about 30 mm Hg to about 55 mm Hg.

Embodiment II-19. The method of any one of Embodiments II-1 to II-18, wherein the trihydrate form is in a crystalline form, and wherein the crystalline form has XRPD peaks at 7.74±0.5° and 20.95±0.5°.

Embodiment II-20. The method of any one of Embodiments II-1 to II-19, wherein at least 100 kg of the free base is combined with the organic solvent to form the mixture.

Embodiment II-21. The method of any one of Embodiments II-1 to II-20, wherein at least 100 kg of precipitate is isolated.

Embodiment II-22. The method of any one of Embodiments II-1 to II-21, wherein at least 100 kg of isolated precipitate is dried.

Embodiment II-23. The method of any one of Embodiments II-1 to II-22, wherein at least 100 kg of the trihydrate form is produced.

Embodiment II-24. The method of any one of Embodiments II-1 to II-23, wherein at least 200 kg of the free base is combined with the organic solvent to form the mixture.

Embodiment II-25. The method of any one of Embodiments II-1 to II-24, wherein at least 200 kg of precipitate is isolated.

Embodiment II-26. The method of any one of Embodiments II-1 to II-25, wherein at least 200 kg of isolated precipitate is dried.

Embodiment II-27. The method of any one of Embodiments II-1 to II-26, wherein at least 200 kg of the trihydrate form is produced.

Embodiment II-28. The method of any one of Embodiments II-1 to II-27, wherein after step (b) and prior to step (c), the mixture is adjusted to comprise water and isopropanol at a volume ratio of less than 3:7.

Embodiment II-29. The method of any one of Embodiments II-1 to II-28, wherein after step (b) and prior to step (c), the mixture is adjusted to comprise water and isopropanol at a volume ratio of less than 1:4.

Embodiment II-30. The method of any one of Embodiments II-1 to II-28, wherein after step (b) and prior to step (c), the mixture is adjusted to comprise water and isopropanol, wherein the water is present at between 5% to 15% by weight.

Embodiment II-31. The method of any one of Embodiments II-1 to II-30, wherein the mixture in step (c) is stirred at a temperature of 40° C. or less to form the precipitate.

Embodiment II-32. The method of any one of Embodiments II-1 to II-31, wherein the mixture in step (c) is stirred at a temperature of 30° C. or less to form the precipitate.

Embodiment II-33. The method of any one of Embodiments II-1 to II-32, wherein after step (d) and before step (e), at least a portion of the isolated precipitate is dissolved in a recrystallization solvent to form a recrystallization mixture, the recrystallization mixture is stirred until a recrystallized precipitate is formed, and the recrystallized precipitate is isolated to form an isolated precipitate.

Embodiment II-34. The method of Embodiment II-33, wherein the recrystallization mixture comprises water and isopropanol at a volume ratio of less than 3:7.

Embodiment II-35. The method of Embodiment II-33, wherein the recrystallization mixture comprises water and isopropanol at a volume ratio of less than 1:4.

Embodiment II-36. The method of Embodiment II-33, wherein the recrystallization mixture comprises water at 5% to 10% by weight.

Embodiment II-37. The method of Embodiment II-33, wherein the recrystallization mixture comprises isopropanol and water, wherein the water is present at 5% to 10% by weight.

Embodiment II-38. The method of any one of Embodiments II-33 or II-37, wherein the recrystallization mixture is stirred at a temperature of 40° C. or less to form the recrystallization precipitate.

Embodiment II-39. The method of any one of Embodiments II-33 or II-37, wherein the recrystallization mixture is stirred at a temperature of 30° C. or less to form the recrystallization precipitate.

Embodiment II-40. The method of any one of Embodiments II-1 to II-39, wherein the isolated precipitate is washed prior to drying.

Embodiment II-41. The method of Embodiment II-40, wherein the isolated precipitate is washed with a wash solvent comprising water and isopropanol at a volume ratio of less than 3:7.

Embodiment II-42. The method of Embodiment II-40 or II-41, wherein the isolated precipitate is washed with a wash solvent comprising water and isopropanol at a volume ratio of less than 1:4.

Embodiment II-43. The method of any one of Embodiments II-1 to II-39, wherein the isolated precipitate is washed with an aqueous wash prior to drying under reduced pressure, wherein the aqueous wash comprises organic solvent and about 5% to about 15% by weight water.

Embodiment II-44. The method of any one of Embodiments II-1 to II-43, wherein the isolated precipitate is dried under reduced pressure until the organic solvent content is less than about 5000 ppm, less than about 4000 ppm, less than about 3000 ppm, or less than about 2000 ppm.

Embodiment II-45. The method of Embodiment II-44, wherein the organic solvent comprises one or more alcohols.

Embodiment II-46. The method of any one of Embodiments 11-2, 11-44, or II-45, wherein the organic solvent comprises one or more $C_1$-$C_8$ alcohols.

Embodiment II-47. The method of any one of Embodiments II-44 to II-46, wherein the organic solvent comprises isopropanol.

Embodiment II-48. The method of any one of Embodiments II-1 to II-47, wherein the isolated precipitate is dried under reduced pressure until the isopropanol content is less than about 6000 ppm.

Embodiment II-49. The method of any one of Embodiments II-1 to II-48, wherein the isolated precipitate is dried under reduced pressure until the isopropanol content is less than about 5000 ppm, less than about 4000 ppm, less than about 3000 ppm, or less than about 2000 ppm.

Embodiment II-50. The method of any one of Embodiments II-1 to II-49, wherein the trihydrate form is in a crystalline form, and wherein the crystalline form has a greater than 50% relative intensity XRPD 2-theta (2θ) peak at 7.74°±0.5°, and a 100% relative intensity XRPD 2-theta (2θ) peak at 20.95°±0.5°.

Embodiment II-51. The method of any one of Embodiments II-1 to II-50, wherein the trihydrate form is in a crystalline form, and wherein the crystalline form has two or more XRPD 2-theta (2θ) peaks selected from the group consisting of 10.3°±0.2°, 13.6°±0.2°, 14.8°±0.2°, 15.0°±0.2°, 15.4°±0.2°, 17.5°±0.2°, 18.3°±0.2°, 18.6°±0.2°, 19.2°±0.2°, 21.3°±0.2°, 22.0°±0.2° 0, 23.6°±0.2°, 24.3°±0.2°, 25.2°±0.2°, 26.0°±0.2°, 27.2°±0.2°, 30.1°±0.2°, 32.4°±0.2°, 33.4°±0.2°, 38.2°±0.20, and 39.4°±0.20.

Embodiment II-52. The method of any one of Embodiments II-1 to II-51, wherein the trihydrate form is in a crystalline form, and wherein the crystalline form has XRPD 2-theta (20) peaks at 7.6°±0.2° and 20.7°±0.2°.

Embodiment II-53. The method of Embodiment II-52, wherein the 7.6°±0.2° XRPD 2-theta (2θ) peak has greater than 50% relative intensity, and the 20.7°±0.2° XRPD 2-theta (20) peak has 100% relative intensity.

Embodiment II-54. The method of Embodiment II-52 or II-53, wherein the crystalline form further has two or more XRPD 2-theta (2θ) peaks selected from the group consisting of 10.3°±0.2°, 13.6°±0.2°, 14.8°±0.2°, 15.0°±0.2°, 15.4°±0.2°, 17.5°±0.2°, 18.3°±0.2°, 18.6°±0.2°, 19.2°±0.2°, 21.3°±0.2°, 22.0°±0.2°, 23.6°±0.2°, 24.3°±0.2°, 25.2°±0.2°, 26.0°±0.2°, 27.2°±0.2°, 30.1°±0.2°, 32.4°±0.2°, 33.4°±0.2°, 38.2°±0.20, and 39.4°±0.20.

Embodiment II-55. A method of treating a gastrointestinal disorder in a subject in need thereof, comprising administering to the subject in need thereof a therapeutically effective amount a trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt, which has the following formula:

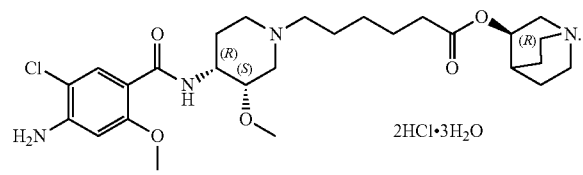

Embodiment II-56. The method of Embodiment II-55, wherein the gastrointestinal disorder is selected from the group consisting of proton pump inhibitor (PPI) resistant GERD, emesis, gastroparesis, opiate induced constipation (OIC), chronic idiopathic constipation (CIC), erosive esophagitis (EE), eosinophilic esophagitis (EoE), functional dyspepsia (FD) or functional motility disorder (FMD), intestinal pseudo-obstruction, irritable bowel syndrome constipation type (IBSc), enteral feeding intolerance (EFI), and post-operative ileus.

Embodiment II-57. The method of Embodiment II-55, wherein the gastrointestinal disorder is selected from the group consisting of post-operative ileus, chronic grass sickness, constipation, megacolon, gastritis, gastrointestinal stasis, and abomasal emptying defect.

EXAMPLES

The following Examples are merely illustrative and are not meant to limit any aspects of the present disclosure in any way.

Example 1: Synthesis of (3S, 4R, 3'R)-6-[4-(4-amino-5-chloro-2-methoxy-benzoylamino)-3-methoxy-piperidin-1-yl]-hexanoic acid 1-azabicyclo [2.2.2]oct-3'-yl ester, dihydrochloride salt, trihydrate A 4,000-L reactor was charged with approximately 250 kg of crude (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester in isopropyl alcohol (300 kg) and water (80 L). Then, under a nitrogen atmosphere, and stirring at 80 rpm, 80 kg of 32% HCl was introduced slowly, keeping the temperature of the mixture below 45° C. and the pH around 4.0. When addition was complete, the solution temperature was cooled to 25° C. and stirring was continued for at least 2 hours until the product precipitated. Then, 800 kg of isopropyl alcohol was charged into the reactor over a period of 2 to 4 hours, and the mixture was stirred for another 90 minutes. The crude precipitate (283 kg) was isolated by centrifugation. The crude product was purified by crystallization in the following manner: Water (100 L) was added to the crude product. Partial vacuum was applied and then the reactor was purged with nitrogen. Agitation was set at 80 rpm, and the temperature of the aqueous mixture was brought to 55° C. The mixture was stirred at 55° C. until the solid was dissolved, then the solution was filtered in order to remove any foreign solid matter. To the solution was added 330 kg of isopropyl alcohol (resulting in approximately 100 L:420 L water: isopropanol). The temperature of the solution was brought to 25° C. and then stirred at 80 rpm for at least 2 hours until the material precipitated. The precipitate was isolated by centrifugation.

The wet dihydrochloride salt (252 kg) was then charged into a cone dryer and the jacket temperature of the dryer set at 30° C. and vacuum (pressure=35 mmHg) was applied for 1 hour 20 minutes. The jacket temperature was then brought to 40° C., still under 35 mmHg of pressure, for 1 hour and 10 minutes. The jacket temperature was then brought to 45° C. for 1 hour. Finally, the jacket temperature was brought to 50° C. until the % water in the product, as measured by Karl Fisher analysis, was 8.0 to 8.4% and the isopropanol content was below 5,000 ppm. After 2 hours at 50° C., water content was 8.46% and isopropanol content was 50,238 ppm. After 5 hours at 50° C., the contents were 8.40% and 1,994 ppm, respectively, and drying was stopped.

Example 2: Dehydration Profile by Thermographic Analysis

Thermographic analysis (TGA) curves were generated for the anhydrate and trihydrate using a Perkin Elmer TGA-7. Three to five milligram samples were weighed into aluminum sample pans and run under dry nitrogen at 5° C./minute from 25° C. to 250° C. The data were exported to Excel to enable plotting. The sample of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester, dihydrochloride salt, trihydrate, exhibited a % loss of 8.2% by 63° C., corresponding to the loss of 3 molecules of water per molecule of compound.

Figure 5:
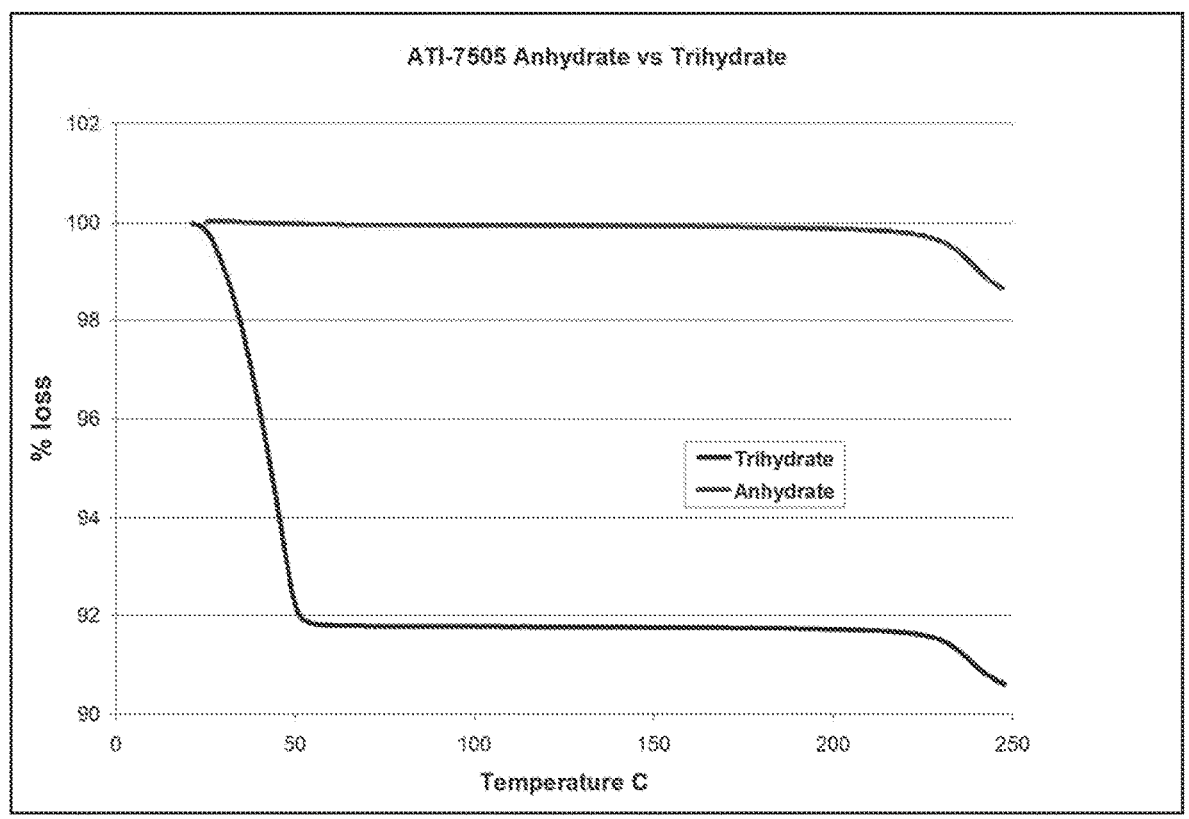
FIG. 5 provides thermographic analysis scans for the anhydrate (top line) and trihydrate (bottom line) forms.

Representative TGA scans for the anhydrate and trihydrate are shown in FIG. 5. The two differ in the appearance of the dehydration mass loss observed for the trihydrate and absent as expected from the anhydrate. Dehydration of the trihydrate started immediately upon start of heating and was complete by approximately 50° C. Complete dehydration below 100° C. is consistent with the assignment of the trihydrate as a channel type hydrate.

Example 3: Water Vapor Sorption Isotherm

Figure 4:
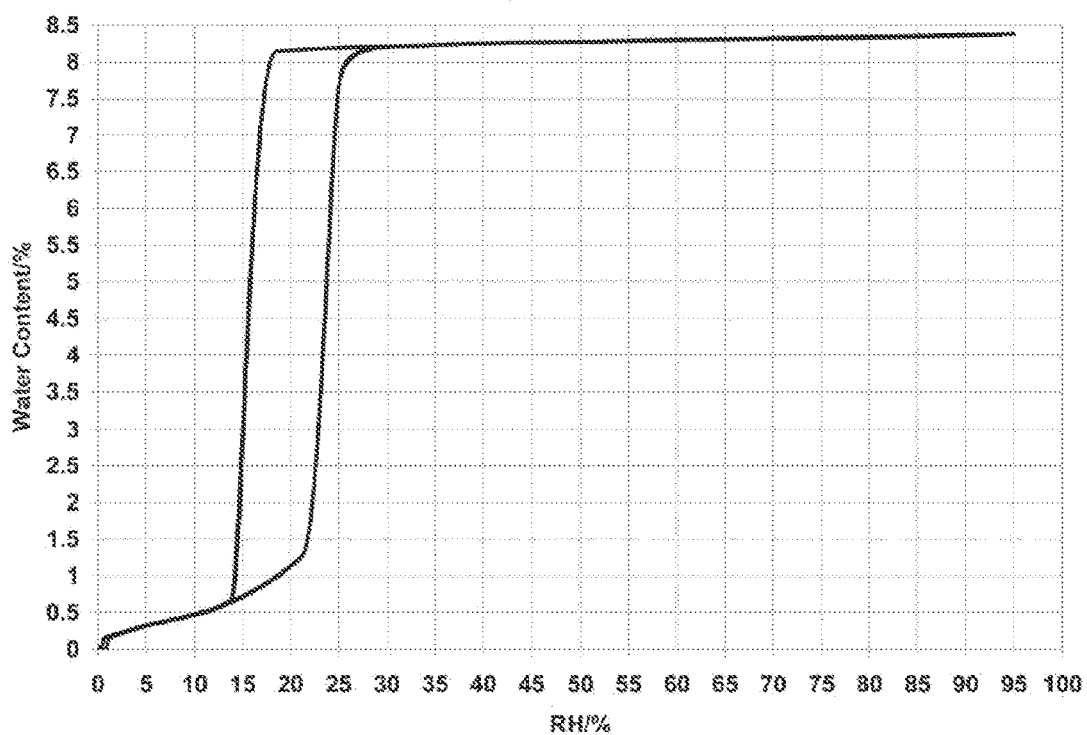
FIG. 4 is a water vapor sorption isotherm of the di-hydrochloride salt at 25° C.

A water vapor isotherm was obtained using a Surface Measurements System DVS-1 equilibrated to 25° C. Approximately 7 mg of the trihydrate compound was spread in a thin layer on a glass sample holder and pre-dried at 0% relative humidity before starting the run. The isotherm was then obtained by scanning the sample from 0% RH to 90% RH and back to 0% RH at a rate of 2% RH per hour. The results are shown FIG. 4.

As shown in the figure, dehydration and rehydration occur quickly across a thin layer of compound. Factors influencing the rate of re-equilibrium include bed depth and/or sample mass, and the magnitude of humidity change from the critical humidity. For example, increasing the bed depth from 1 millimeter to 7 millimeter resulted in a change of rate for dehydration or rehydration. Re-equilibrium was established within minutes for the 1 mm layer but required hours for the 7 mm layer, when 0% RH and 55% RH were used as the humidity drivers. If relative humidities (RH) closer to the critical RH (15-20% RH) had been chosen, it is expected that the re-equilibration times would have been longer over all.

The critical relative humidity increased with increasing temperature. Minimum relative humidities required to maintain the trihydrate were: 20% RH (25° C.), 25% RH (40° C.), 30% RH (50° C.), and 50% RH (60° C.). Use of very high humidities at elevated temperatures to maintain the hydrate may not be advisable as deliquescence was observed at 100% RH for temperatures of 40° C. and above.

Example 4: X-Ray Powder Diffraction

X-ray powder diffraction (XRPD) was performed on samples of the anhydrous form and the trihydrate using a Bruker D5000 X-ray diffractometer. The D5000 was equipped with a 2.2 kW Cu anode x-ray tube, an Anton Parr TTK-1 low temperature stage and high speed position sensitive detector (PSD). Cu Kα radiation (λ=1.5418 Å) was used to obtain all powder patterns. A dual foil, nickel filter was placed in the receiving path of the X-rays to remove the Kβ radiation. Material was mounted and analyzed on a front loading sample holder. Scans were performed over the range of below 4° to 40° 2-theta (2θ), at a 0.02° step size for 0.2 and 0.5 seconds per step.

Figure 3:
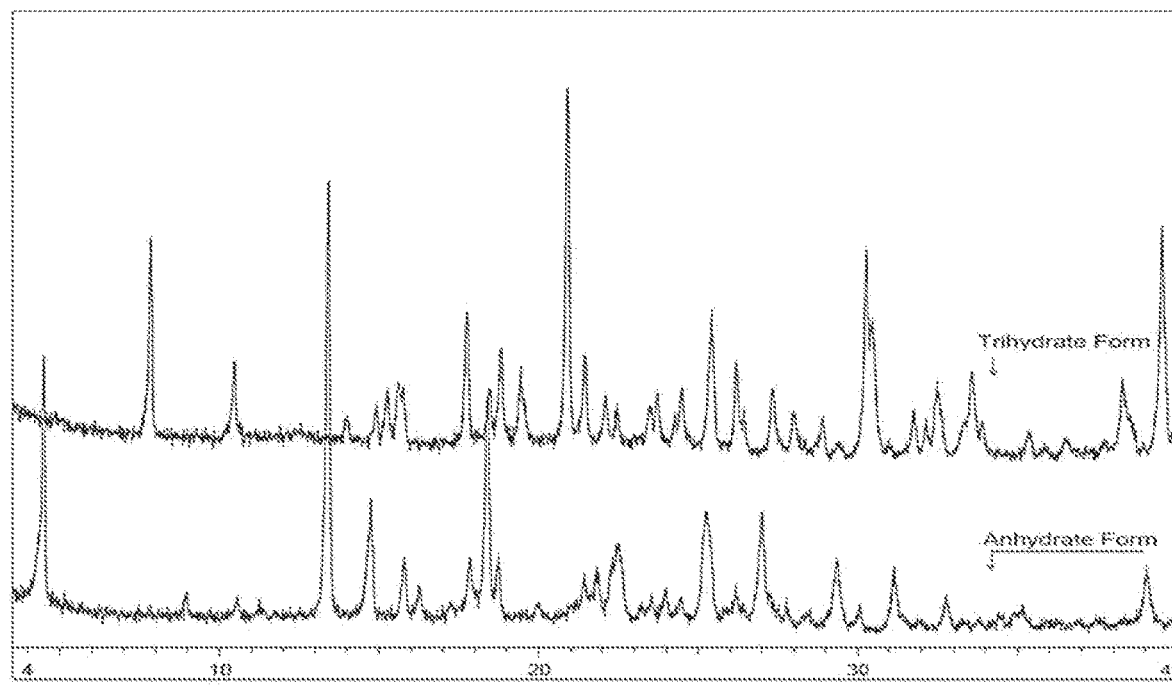
FIG. 3 are X-ray powder diffraction (XRPD) patterns of the anhydrate (bottom) and the trihydrate (top) forms of the (3S, 4R, 3'R)-6-[4-(4-amino-5-chloro-2-methoxy-benzoylamino)-3-methoxy-piperidin-1-yl]-hexanoic acid 1-azabi-cyclo[2.2.2]oct-3'-yl ester di-hydrochloride salt.

Representative XRPD patterns for the anhydrate and trihydrate forms are shown in FIG. 3. Each form is a unique crystalline phase as is evident by the individual diffraction patterns. The anhydrate form exhibits major specific peaks at 4.55°±0.5° (>50% relative intensity), and at 13.5° 0±0.5°, the latter being the most intense peak (100% relative intensity).

The trihydrate form exhibits major specific peaks at 7.74°±0.5° (>50% relative intensity), and at 20.9° 5±0.5°, the latter being the most intense peak (100% relative intensity). A more detailed peak list for the trihydrate from XRPD analyses includes (in degrees 2-theta (2θ)) approximately 7.6°±0.2°, 10.3°±0.2°, 13.6°±0.2°, 14.8°±0.2°, 15.0°±0.2°, 15.4°±0.2°, 17.5°±0.2°, 18.3°±0.2°, 18.6°±0.2°, 19.2° 0.2° 0, 20.7° 0.20, 21.3°±0.2°, 22.0°±0.2°, 23.6°±0.2°, 24.3°±0.2°, 25.2°±0.2°, 26.0°±0.2°, 27.2°±0.2°, 30.1°±0.2°, 32.4°±0.2°, 33.4°±0.2°, 38.2°±0.2°, 39.4°±0.2°.

During dehydration and rehydration of the trihydrate, no transitional state was observed, rather the material exists in either one form or the other depending on the amount of water retained in each individual crystal. During in-situ dehydration and re-hydration, both forms were observed in the same pattern, at varying levels.

Figure 6:
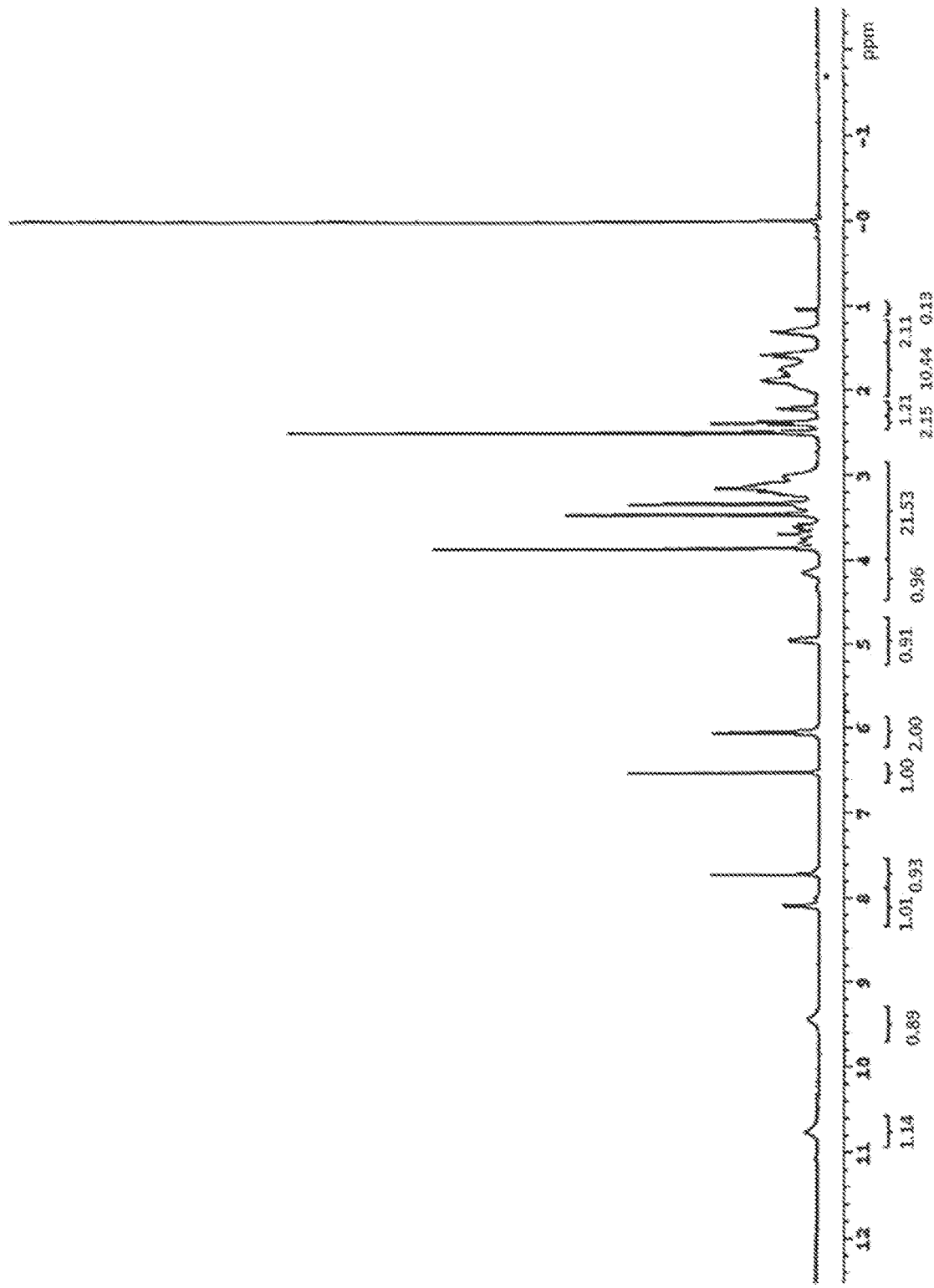
FIG. 6 is a representative $^1$H-NMR spectrum of the trihydrate form.

Example 5: NMR Characterization of the Trihydrate $^1$H-Nuclear Magnetic Resonance Spectroscopy ($^1$H-NMR): Approximately 6 mg of the trihydrate was dissolved in in 1 g of deuterated solvent (dimethylsulfoxide (DMSO)-C45 99.9% d, with 0.05% v/v tetramethylsilane (TMS)). A Varian Gemini 300 MHz FT-NMR spectrometer was used to obtain the $^1$H-NMR spectrum. A list of the peaks is provided in Table 1 below. A representative $^1$H-NMR spectrum is provided in FIG. 6.

TABLE 1

$^1$H-NMR peak list for trihydrate

| Chemical Shift (ppm) | Peak Type | Integral |
| --- | --- | --- |
| 10.76 | broad singlet | 1.14 |
| 9.44 | broad singlet | 0.89 |
| 8.11, 8.51 | Broad doublet | 1.01 |
| 7.72 | singlet | 0.93 |
| 6.53 | singlet | 1.00 |
| 6.06 | broad singlet | 2.00 |
| 4.97, 4.96, 4.94 | broad multiplet | 0.91 |
| ~4.20-~4.10 | broad multiplet | 0.96 |
| 3.86 | singlet | 21.53 |
| 3.79, 3.75 | broad multiplet | |
| 3.69 | broad peak | |
| 3.65, 3.62, 3.60, 3.57 | doublet, doublet | |
| 3.46 | singlet | |
| ~3.38 | broad peak | |
| 3.34 | singlet | |
| ~3.24-~3.08 | overlapping multiplets | |
| ~3.08-~2.96 | broad peak | |
| 2.42, 2.39, 2.37 | triplet | 2.15 |
| ~2.24-~2.18 | broad multiplet | 1.21 |
| ~2.02-~1.64 | overlapping multiplets | 10.44 |
| 1.63, 1.61, 1.58, 1.56, 1.53 | triplet, triplet | |
| 1.35, 1.33, 1.30, 1.28, ~1.25 | triplet, triplet | 2.11 |
| 1.05, 1.03 | doublet | 0.13 |
| 0.00 | singlet | NA (TMS) |

Figure 7:
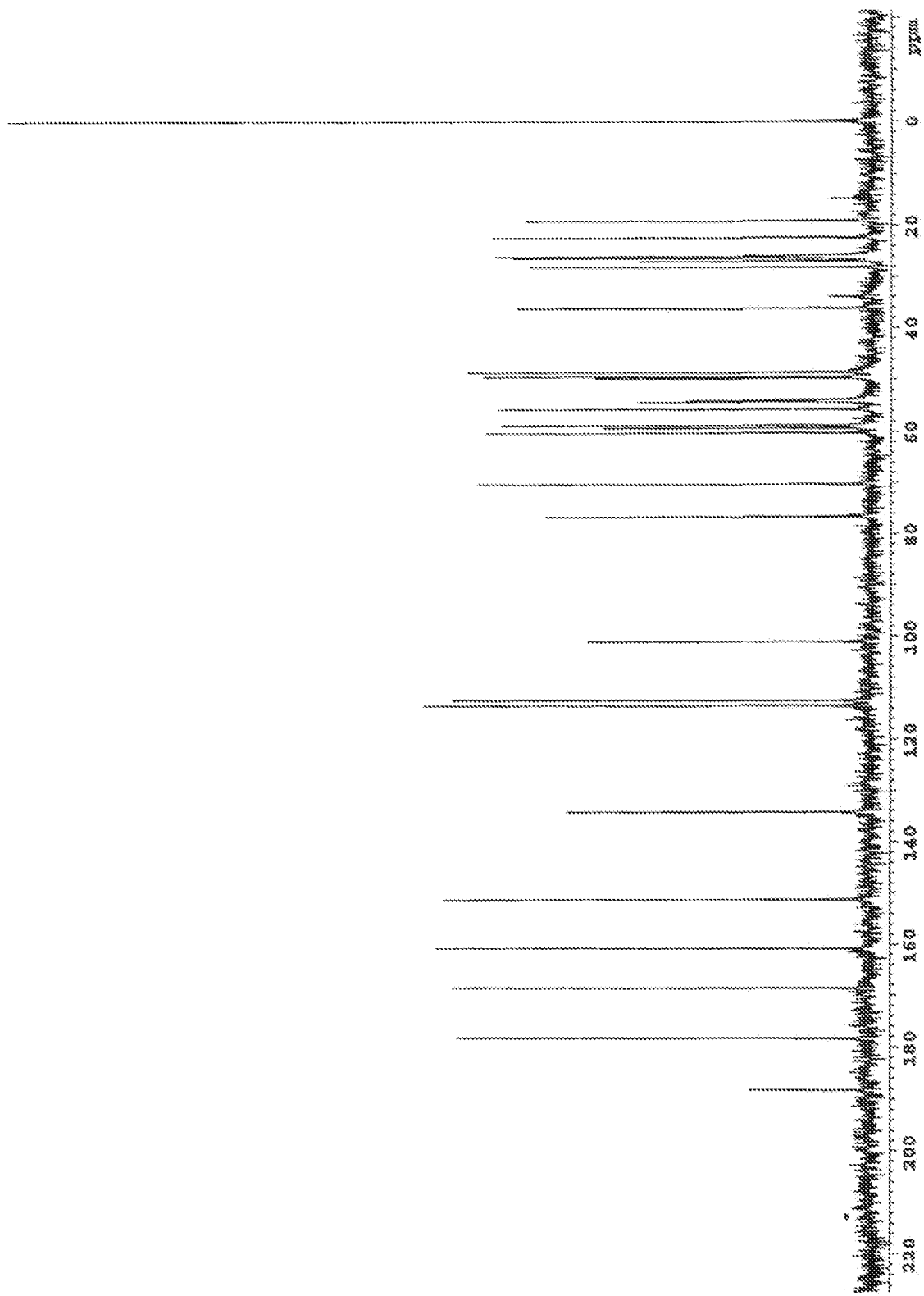
FIG. 7 is a representative $^{13}$C-NMR spectrum of the trihydrate form.

$^{13}$C-Nuclear Magnetic Resonance Spectroscopy ($^{13}$C-NMR): Approximately 46 mg of the trihydrate was dissolved in 1 mL of deuterated solvent (deuterium oxide, Aldrich, 99.900 D, TPAS 0.750%). The $^{13}$C-NMR spectrum was obtained using a Varian Gemini 300 MHz FT-NMR spectrometer. A list of the peaks is provided in Table 2 below. A representative $^{13}$C-NMR spectrum is provided in FIG. 7.

TABLE 2

$^{13}$C-NMR peak list for trihydrate

| Chemical Shift (ppm) | Relative Peak Height |
| --- | --- |
| 188.305 | NA (TPAS) |
| 178.368 | 81 |
| 68.659 | 82 |
| 160.787 | 85 |
| 151.267 | 84 |
| 134.247 | 59 |
| 113.575 | 88 |
| 112.604 | 82 |
| 101.171 | 55 |
| 76.757 | 63 |
| 70.297 | 77 |
| 60.322 | 75 |
| 59.350 | 52 |
| 58.834 | 72 |
| 55.736 | 73 |
| 54.355 | 45 |
| 54.051 | 36 |
| 49.845 | 53 |
| 49.473 | 76 |
| 48.638 | 79 |
| 36.241 | 69 |
| 28.179 | 67 |
| 26.965 | 45 |
| 26.411 | 70 |
| 26.168 | 74 |
| 25.978 | 66 |
| 22.395 | 64 |
| 19.168 | 67 |
| 0.000 | NA (TPAS) |

Example 6: 12-Month Stability of the Anhydrous Form of the Dihydrochloride Salt Under Controlled Temperature and Humidity The dihydrochloride salt, anhydrous form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester, was placed in stability chambers with temperature and humidity controlled, for up to 12 months. The temperature was set at 25° C., and the relative humidity was set at 60%. The samples were assayed at time zero, then at 3, 6, 9, and 12 months using an HPLC method. The HPLC conditions were as follows:

Column: Inertsil C8-3, 250 mm length, 3 mm diameter, 5 um particle size
Mobile Phase A: 2000 mL water+3 mL formic acid
Mobile Phase B: 1000 mL methanol+3 mL formic acid
Flow rate: 0.6 mL/min
Detection wavelength: 275 nm
Injection volume: 20 uL
Time: 50 minutes The results are shown in Table 3 below. Although the purity of the compound remained within the specifications originally set for the active material (Purity HPLC Area %), the strength of the active pharmaceutical ingredient (API) decreased over time due to an increase in the water content (from 0.45% at time zero to 8.47% at 6 months, and then stable up to 12 months). This is an approximately 8% decrease in strength of the active ingredient, which puts the product out of the acceptable range of Good Manufacturing Practice (GMP) release specifications originally set for this material.

TABLE 3

Stability of the Anhydrate form of the Dihydrochloride Salt at 25° C./60% RH

| Time (months) | 0 | 3 | 6 | 9 | 12 |
|---|---|---|---|---|---|
| Purity HPLC (Area %) | 99.3 | 99.2 | 99.3 | 99.2 | 99.3 |
| Water Content | 0.45% | 6.47% | 8.47% | 8.20% | 8.43% |

Example 7: 36-Month Stability of the Trihydrate Form of the Dihydrochloride Salt Under Strictly Controlled Conditions of Temperature and Humidity The trihydrate form of the dihydrochloride salt of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester, was placed in stability chambers with temperature and humidity control for up to 36 months. The temperature was set at 25° C., and the relative humidity was set at 60%. The samples were assayed at time zero, then at 3, 6, 9, 12, 18, 24, and 36 months using an HPLC method as described in the example above. The results are shown in Table 4 below.

The results show that the trihydrate form is stable for at least 36 months with regard to both purity and strength. The water content of the API did not change for up to 36 months. This batch of material would pass GMP certification for use in humans after 36 months following synthesis of the API.

Example 8: Stability of the Trihydrate Form of the Dihydrochloride Salt when Stored in Bulk in a GMP Storage Facility The trihydrate form was evaluated for stability with regard to purity and strength over a time period of up to 11 years, by storing it in a GMP facility under controlled conditions of temperature and relative humidity (temperature=room temperature and relative humidity>30%). Results are presented in Table 5 below.

TABLE 5

Stability of the Trihydrate form of the Dihydrochloride Salt when stored in bulk at Room Temperature and RH >30%

| | Year Tested | | |
|---|---|---|---|
| | 2007 | 2018 (Drum #1) | 2018 (Drum #2) |
| Purity HPLC (Area %) | 99.6 | 99.6 | 99.6 |
| Water Content | 8.8% | 8.4% | 8.7% |

These results demonstrate that the trihydrate form of the API is stable under GMP storage when stored under the temperature and humidity conditions that are usually applied in GMP storage facilities.

Example 9: Polymorph Screen

A polymorph screen was performed on the anhydrous dihydrochloride salt of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester, by recrystallizing the material under approximately 90 different crystal growth conditions and analyzing the recovered solids using X-ray powder diffraction (XRPD). A secondary screen was performed using noncompetitive slurry experiments followed by X-ray diffraction of the solids. From this screen, three different solid-state crystal forms of the anhydrous salt were identified (Form I, Form II, and Form III), and a solid-state crystal form of the trihydrate was identified (Form IV). An amorphous form was also identified. Further, it was discovered that Form I could be converted to Form IV under certain conditions.

The crystal growth or desaturation conditions for the recrystallization panels are summarized in Table 6 below. Each recrystallization panel contained 22-32 wells, with each well containing different solvent compositions. The solvent matrices used for the three panels of the polymorph screen and the conditions of the screens are provided in

TABLE 4

Stability of the Trihydrate form of the Dihydrochloride Salt at 25° C./60% RH

| Time (months) | 0 | 3 | 6 | 9 | 12 | 18 | 24 | 36 |
|---|---|---|---|---|---|---|---|---|
| Purity HPLC (Area %) | 99.8 | 100.2 | 100 | 99.9 | 99.1 | 100 | 99.6 | 99.5 |
| Water Content | 8.5% | 8.6% | 8.6% | 8.4% | 8.4% | 8.6% | 8.6% | 8.6% |

Tables 7, 8, and 9, which also list the resulting crystalline form of each crystallization experiment based on X-ray diffraction data.

TABLE 6

Summary of Solvent Recrystallization Panels.

| Panel | No. of Experiments (No. of wells) | Scale (mL) | Saturation Temperature (° C.) | Growth Temperature (° C.) | Nitrogen Flow Rate (psig) |
|---|---|---|---|---|---|
| I | 22 | 5-10 | 40 | 40 | 5 |
| II | 32 | 10 | 30 | 30 | 7 |
| III | 32 | 10 | 50 | 50 | 10 |

TABLE 7

Panel I Matrix (Saturation/Growth Temperature = 40° C.). Top half of panel lists solvent ratios as solvent:cosolvent. Results of the panel are in the bottom half.

| Well | Solvent System | Solvent Volume (mL) | Solute Mass (mg) | Recovered Solids | Form |
|---|---|---|---|---|---|
| 1 | methanol | 5 | 250 | white/brown | amorphous |
| 2 | ethanol | 10 | 100 | tannish | Form 1 |
| 3 | 1 propanol | 10 | 50 | tannish | Form IV |
| 4 | ethylene glycol | 10 | 100 | | amorphous |
| 5 | water | 10 | 150 | brownish | amorphous |
| 6 | MEK | 10 | 50 | tannish | insol |
| 7 | methylene chloride | 10 | 50 | | insol |
| 8 | chloroform | 10 | 50 | tannish | insol |
| 9 | acetone | 10 | 50 | | insol |
| 10 | 2 propanol | 10 | 50 | | Form 1 |
| 11 | 1 butanol | 10 | 50 | | Form 1 |
| 12 | DMF | 10 | 50 | tannish | Form 1 |
| 13 | DMA | 10 | 50 | yellowish | |
| 14 | butyl amine | 10 | 150 | brownish | gel w/needles |
| 15 | MTBE | 10 | 50 | | insol |
| 16 | isopropyl acetate | 10 | 50 | | insol |
| 17 | nitromethane | 10 | 50 | tannish | Form 1 |
| 18 | isopropyl ether | 10 | 50 | | insol |
| 19 | EtOAc | 10 | 25 | | insol |
| 20 | acetonitrile | 10 | 25 | white | Form 1 |
| 21 | toluene | 10 | 25 | | insol |
| 22 | heptane | 10 | 25 | | insol |

TABLE 8

Panel II Matrix (Saturation/Growth Temperature = 30° C.). Top half of panel lists solvent ratios as solvent:cosolvent. Results of the panel are in the bottom half.

| Solvent | | 1 | 2 | 3 | 4 | CoSolvent |
|---|---|---|---|---|---|---|
| EtOH | A | 9:1 | 7:3 | 3:7 | 1:9 | water |
| MeOH | B | 9:1 | 7:3 | 3:7 | 1:9 | 1-propanol |
| Water | C | 9:1 | 7:3 | 3:7 | 1:9 | 2-propanol |
| butyl amine | D | 9:1 | 7:3 | 3:7 | 1:9 | 1-butanol |
| 1-propanol | E | 9:1 | 7:3 | 3:7 | 1:9 | ACN |
| EtOH | F | 9:1 | 7:3 | 3:7 | 1:9 | 1-propanol |
| DMF | G | 9:1 | 7:3 | 3:7 | 1:9 | toluene |
| DMA | H | 9:1 | 7:3 | 3:7 | 1:9 | nitromethane |
| EtOH | A | Form II | am | am | am | water |
| MeOH | B | Form II | Form II | Form II + IV | Form IV | 1-propanol |
| Water | C | am | am | am | Form IV | 2-propanol |
| butyl amine | D | gel | gel | gel | gel | 1-butanol |
| 1-propanol | E | Form IV | Form II | Form IV | Form IV | ACN |
| EtOH | F | Form IV | Form IV | Form IV | Form IV | 1-propanol |
| DMF | G | Form IV | Form I | gel | insol | toluene |
| DMA | H | | Form IV | Form IV | Form IV | nitromethane |

TABLE 9

Panel III Matrix (Saturation/Growth Temperature = 50° C.). Top half of panel lists solvent ratios as solvent:cosolvent. Results of the panel are in the bottom half.

| Solvent | | 1 | 2 | 3 | 4 | CoSolvent |
|---|---|---|---|---|---|---|
| EtOH | A | 9:1 | 7:3 | 3:7 | 1:9 | water |
| MeOH | B | 9:1 | 7:3 | 3:7 | 1:9 | 1-propanol |
| Water | C | 9:1 | 7:3 | 3:7 | 1:9 | 2-propanol |
| DMF | D | 9:1 | 7:3 | 3:7 | 1:9 | methanol |
| 1-propanol | E | 9:1 | 7:3 | 3:7 | 1:9 | ACN |
| EtOH | F | 9:1 | 7:3 | 3:7 | 1:9 | 1-propanol |
| DMF | G | 9:1 | 7:3 | 3:7 | 1:9 | toluene |
| DMA | H | 9:1 | 7:3 | 3:7 | 1:9 | nitromethane |
| EtOH | A | III + am | am | am | am | water |
| MeOH | B | am | II | II | I | 1-propanol |
| Water | C | am | am | am | II | 2-propanol |
| DMF | D | III + am | II | III | III | methanol |
| 1-propanol | E | I | I | I + am | I | ACN |
| EtOH | F | am | II + I | I | I | 1-propanol |
| DMF | G | IV | II | insol | insol | toluene |
| DMA | H | low sol | IV | I | I | nitromethane |

Noncompetitive Slurry Experiments for Polymorph Screening: Noncompetitive slurry experiments were performed as a supplemental polymorph screening method. When suspensions of a polymorphic material are prepared, any polymorphic form with a lower solubility (more thermodynamically stable form) can nucleate. The nucleated forms can convert all the residual solids to the nucleated form via solvent-mediated phase transition. Suspensions of the isolated Form I were prepared by adding excess solid to several different solvent systems. The suspensions were stirred vigorously at ambient temperature for 3 weeks. The remaining solids were collected by vacuum filtration and analyzed by powder X-ray diffraction to determine if any changes in the crystalline form of the solids occurred. The results of the noncompetitive slurry work are shown in Table 10 below.

TABLE 10

Summary of Noncompetitive Slurry Experiments

| Solvent | Antisolvent | Temperature | Resulting Form |
|---|---|---|---|
| 1-Propanol | Water | Ambient | Form 1 |
| Ethanol | Water | Ambient | Form 1 |
| Methanol | Water | Ambient | Form 1 |
| Water | Water | Ambient | Form 1 |
| Acetonitrile | Water | Ambient | Form 1 |

Based on the outcome of the slurry experiments, it was determined that Form I is the most thermodynamically stable anhydrous form.

The recrystallization data in Table 8 (Panel II) shows that the trihydrate Form IV can be obtained by recrystallization from a water:2-propanol solvent mixture at a ratio of less than 3:7 by volume (less than 30% water and 70% isopropanol by volume) and at a temperature not exceeding 40° C. Certain solvents used in the experiments, such as DMA and DMF, can be difficult to remove from compositions (such as bulk compositions) due to their high boiling point. In some situations, trying to remove these high boiling solvents from a composition requires conditions that can be destabilizing to the desired compound, such as requiring heating in combination with very low pressure.

What is claimed is:

1. A method of improving gastrointestinal motility in a subject in need thereof, the method comprising administering a therapeutically effective amount of a crystalline form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt to the subject, wherein the crystalline form is characterized by XRPD 2θ peaks at 7.74±0.5° and 20.95±0.5°.

2. The method of claim 1, wherein the subject in need thereof has a gastrointestinal disorder.

3. The method of claim 2, wherein the gastrointestinal disorder is selected from the group consisting of gastroesophageal reflux disease (GERD), functional dyspepsia, functional motility disorder, gastroparesis, paralytic ileus, post-operative ileus, intestinal pseudo-obstruction, irritable bowel syndrome (IBS), constipation, enteral feeding intolerance (EFI), esophagitis, megacolon, gastritis, gastrointestinal stasis, and abomasal emptying defect.

4. The method of claim 2, wherein the gastrointestinal disorder is selected from the group consisting of gastroesophageal reflux disease (GERD), functional dyspepsia, functional motility disorder, gastroparesis, paralytic ileus, post-operative ileus, intestinal pseudo-obstruction, irritable bowel syndrome (IBS), constipation, enteral feeding intolerance (EFI), and esophagitis.

5. The method of claim 2, wherein the gastrointestinal disorder is selected from the group consisting of post-operative ileus, constipation, megacolon, gastritis, gastrointestinal stasis, and abomasal emptying defect.

6. The method of claim 1, wherein the crystalline form is a trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt, which has the following formula:

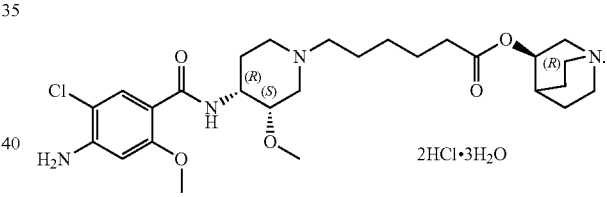

2HCl•3H$_2$O

7. The method of claim 1, wherein the crystalline form is further characterized by one or more XRPD 2θ peaks selected from the group consisting of 10.3°±0.2°, 13.6°±0.2°, 14.8°±0.2°, 15.0°±0.2°, 15.4°±0.2°, 17.5°±0.2°, 18.3°±0.2°, 18.6°±0.2°, 19.2°±0.2°, 21.3°±0.2°, 22.0°±0.2° 23.6°±0.2°, 24.3°±0.2°, 25.2°±0.2°, 26.0°±0.2°, 27.2°±0.2°, 30.1°±0.2°, 32.4°±0.2°, 33.4°±0.2°, 38.2°±0.2°, and 39.4°±0.2°.

8. The method of claim 1, wherein the crystalline form is further characterized by two or more XRPD 2θ peaks selected from the group consisting of 10.3°±0.2°, 13.6°±0.2°, 14.8°±0.2°, 15.0°±0.2°, 15.4°±0.2°, 17.5°±0.2°, 18.3°±0.2°, 18.6°±0.2°, 19.2°±0.2°, 21.3°±0.2°, 22.0°±0.2° 23.6°±0.2°, 24.3°±0.2°, 25.2°±0.2°, 26.0°±0.2°, 27.2°±0.2°, 30.1°±0.2°, 32.4°±0.2°, 33.4°±0.2°, 38.2°±0.2°, and 39.4°±0.2°.

9. The method of claim 1, wherein the crystalline form is further characterized by three or more XRPD 2θ peaks selected from the group consisting of 10.3°±0.2°, 13.6°±0.2°, 14.8°±0.2°, 15.0°±0.2°, 15.4°±0.2°, 17.5°±0.2°, 18.3°±0.2°, 18.6°±0.2°, 19.2°±0.2°, 21.3°±0.2°, 22.0°±0.2° 23.6°±0.2°, 24.3°±0.2°, 25.2°±0.2°, 26.0°±0.2°, 27.2°±0.2°, 30.1°±0.2°, 32.4°±0.2°, 33.4°±0.2°, 38.2°±0.2°, and 39.4°±0.2°.

10. The method of claim 1, wherein the crystalline form is further characterized by an XRPD 2θ peak at 10.3°±0.20.

11. The method of claim 1, wherein the crystalline form is further characterized by an XRPD 2θ peak at 30.1°±0.2°.

12. The method of claim 1, wherein the crystalline form is further characterized by an XRPD 2θ peak at 39.4°±0.2°.

13. The method of claim 1, wherein the crystalline form is further characterized by XRPD 2θ peaks at 10.3°±0.2°, 30.1°±0.2°, and 39.4°±0.2°.

14. A method of treating a gastrointestinal disorder in a subject in need thereof, the method comprising administering a therapeutically effective amount of a crystalline form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt to the subject, wherein the crystalline form is characterized by XRPD 2θ peaks at 7.74±0.5° and 20.95±0.5° and the gastrointestinal disorder is selected from the group consisting of gastroesophageal reflux disease (GERD), functional dyspepsia, functional motility disorder, gastroparesis, paralytic ileus, post-operative ileus, intestinal pseudo-obstruction, irritable bowel syndrome (IBS), constipation, enteral feeding intolerance (EFI), esophagitis, megacolon, gastritis, gastrointestinal stasis, and abomasal emptying defect.

15. The method of claim 14, wherein the gastrointestinal disorder is selected from the group consisting of gastroesophageal reflux disease (GERD), functional dyspepsia, functional motility disorder, gastroparesis, paralytic ileus, post-operative ileus, intestinal pseudo-obstruction, irritable bowel syndrome (IBS), constipation, enteral feeding intolerance (EFI), and esophagitis.

16. The method of claim 14, wherein the gastrointestinal disorder is selected from the group consisting of post-operative ileus, constipation, megacolon, gastritis, gastrointestinal stasis, and abomasal emptying defect.

17. The method of claim 14, wherein the crystalline form is a trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt, which has the following formula:

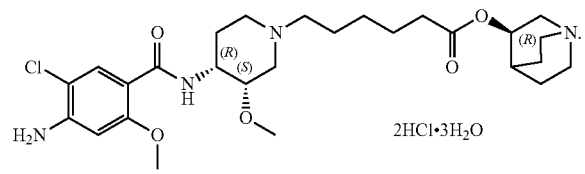

18. The method of claim 14, wherein the crystalline form is further characterized by one or more XRPD 2θ peaks selected from the group consisting of 10.3°±0.2°, 13.6°±0.2°, 14.8°±0.2°, 15.0°±0.2°, 15.4°±0.2°, 17.5°±0.2°, 18.3°±0.2°, 18.6°±0.2°, 19.2°±0.2°, 21.3°±0.2°, 22.0°±0.2° 23.6°±0.2°, 24.3°±0.2°, 25.2°±0.2°, 26.0°±0.2°, 27.2°±0.2°, 30.1°±0.2°, 32.4°±0.2°, 33.4°±0.2°, 38.2°±0.2°, and 39.4°±0.2°.

19. The method of claim 14, wherein the crystalline form is further characterized by two or more XRPD 2θ peaks selected from the group consisting of 10.3°±0.2°, 13.6°±0.2°, 14.8°±0.2°, 15.0°±0.2°, 15.4°±0.2°, 17.5°±0.2°, 18.3°±0.2°, 18.6°±0.2°, 19.2°±0.2°, 21.3°±0.2°, 22.0°±0.2° 23.6°±0.2°, 24.3°±0.2°, 25.2°±0.2°, 26.0°±0.2°, 27.2°±0.2°, 30.1°±0.2°, 32.4°±0.2°, 33.4°±0.2°, 38.2°±0.2°, and 39.4°±0.2°.

20. The method of claim 14, wherein the crystalline form is further characterized by three or more XRPD 2θ peaks selected from the group consisting of 10.3°±0.2°, 13.6°±0.2°, 14.8°±0.2°, 15.0°±0.2°, 15.4°±0.2°, 17.5°±0.2°, 18.3°±0.2°, 18.6°±0.2°, 19.2°±0.2°, 21.3°±0.2°, 22.0°±0.2° 23.6°±0.2°, 24.3°±0.2°, 25.2°±0.2°, 26.0°±0.2°, 27.2°±0.2°, 30.1°±0.2°, 32.4°±0.2°, 33.4°±0.2°, 38.2°±0.2°, and 39.4°±0.2°.

21. The method of claim 14, wherein the crystalline form is further characterized by an XRPD 2θ peak at 10.3°±0.20.

22. The method of claim 14, wherein the crystalline form is further characterized by an XRPD 2θ peak at 30.1°±0.2°.

23. The method of claim 14, wherein the crystalline form is further characterized by an XRPD 2θ peak at 39.4°±0.2°.

24. The method of claim 14, wherein the crystalline form is further characterized by XRPD 2θ peaks at 10.3°±0.2°, 30.1°±0.2°, and 39.4°±0.2°.

25. A method of improving gastrointestinal motility in a subject in need thereof, the method comprising administering a therapeutically effective amount of a crystalline form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt to the subject, wherein the crystalline form is characterized by an XRPD pattern as shown in the FIG. 3 top trace.

26. The method of claim 25, wherein the subject in need thereof has a gastrointestinal disorder.

27. The method of claim 26, wherein the gastrointestinal disorder is selected from the group consisting of gastroesophageal reflux disease (GERD), functional dyspepsia, functional motility disorder, gastroparesis, paralytic ileus, post-operative ileus, intestinal pseudo-obstruction, irritable bowel syndrome (IBS), constipation, enteral feeding intolerance (EFI), esophagitis, megacolon, gastritis, gastrointestinal stasis, and abomasal emptying defect.

28. The method of claim 26, wherein the gastrointestinal disorder is selected from the group consisting of gastroesophageal reflux disease (GERD), functional dyspepsia, functional motility disorder, gastroparesis, paralytic ileus, post-operative ileus, intestinal pseudo-obstruction, irritable bowel syndrome (IBS), constipation, enteral feeding intolerance (EFI), and esophagitis.

29. The method of claim 26, wherein the gastrointestinal disorder is selected from the group consisting of post-operative ileus, constipation, megacolon, gastritis, gastrointestinal stasis, and abomasal emptying defect.

30. The method of claim 25, wherein the crystalline form is a trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt, which has the following formula:

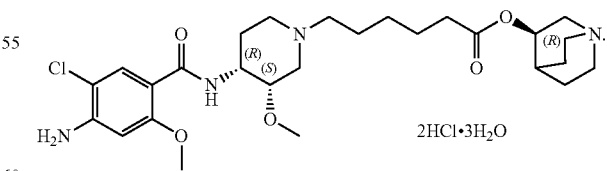

31. A method of treating a gastrointestinal disorder in a subject in need thereof, the method comprising administering a therapeutically effective amount of a crystalline form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt to the subject, wherein the crystalline form is characterized by an XRPD pattern as shown in the FIG. 3 top trace and the gastrointestinal disorder is selected from the group consisting of gastroesophageal reflux disease (GERD), functional dyspepsia, functional motility disorder, gastroparesis, paralytic ileus, post-operative ileus, intestinal pseudo-obstruction, irritable bowel syndrome (IBS), constipation, enteral feeding intolerance (EFI), esophagitis, megacolon, gastritis, gastrointestinal stasis, and abomasal emptying defect.

32. The method of claim 31, wherein the gastrointestinal disorder is selected from the group consisting of gastroesophageal reflux disease (GERD), functional dyspepsia, functional motility disorder, gastroparesis, paralytic ileus, post-operative ileus, intestinal pseudo-obstruction, irritable bowel syndrome (IBS), constipation, enteral feeding intolerance (EFI), and esophagitis.

33. The method of claim 31, wherein the gastrointestinal disorder is selected from the group consisting of post-operative ileus, constipation, megacolon, gastritis, gastrointestinal stasis, and abomasal emptying defect.

34. The method of claim 31, wherein the crystalline form is a trihydrate form of (3S, 4R, 3'R)-6-[4-(4-amino-5-chloro-2-methoxy-benzoylamino)-3-methoxy-piperidin-1-yl]-hexanoic acid 1-azabicyclo[2.2.2]oct-3'-yl ester di-hydrochloride salt, which has the following formula:

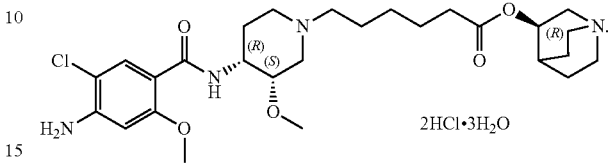

* * * * *